United States Patent
Betancort et al.

(10) Patent No.: US 11,679,106 B2
(45) Date of Patent: *Jun. 20, 2023

(54) BROMODOMAIN INHIBITOR

(71) Applicant: CELGENE QUANTICEL RESEARCH, INC., San Diego, CA (US)

(72) Inventors: Juan Manual Betancort, San Diego, CA (US); Jeffrey Alan Stafford, San Diego, CA (US); Ryan Stansfield, San Diego, CA (US); James Marvin Veal, Apex, NC (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/870,898

(22) Filed: May 9, 2020

(65) Prior Publication Data

US 2020/0338065 A1 Oct. 29, 2020

Related U.S. Application Data

(60) Division of application No. 15/788,741, filed on Oct. 19, 2017, now Pat. No. 10,702,517, which is a continuation-in-part of application No. 15/136,761, filed on Apr. 22, 2016, now abandoned.

(60) Provisional application No. 62/410,756, filed on Oct. 20, 2016, provisional application No. 62/151,205, filed on Apr. 22, 2015.

(51) Int. Cl.
| | | |
|---|---|---|
| *A61K 31/472* | (2006.01) | |
| *A61K 47/32* | (2006.01) | |
| *A61K 47/38* | (2006.01) | |
| *A61K 9/16* | (2006.01) | |
| *A61K 9/20* | (2006.01) | |
| *A61P 35/00* | (2006.01) | |
| *C07D 217/12* | (2006.01) | |
| *C07D 217/24* | (2006.01) | |
| *A61K 9/10* | (2006.01) | |

(52) U.S. Cl.
CPC ............ *A61K 31/472* (2013.01); *A61K 9/10* (2013.01); *A61K 9/1635* (2013.01); *A61K 9/1652* (2013.01); *A61K 9/2054* (2013.01); *A61K 47/32* (2013.01); *A61K 47/38* (2013.01); *A61P 35/00* (2018.01); *C07D 217/12* (2013.01); *C07D 217/24* (2013.01); *A61K 9/1694* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 9,034,900 B2 | 5/2015 | Bennett et al. | |
| 10,166,227 B2 | 1/2019 | Cho | |
| 11,464,771 B2* | 10/2022 | Cho | ........ A61K 38/15 |
| 2007/0213323 A1 | 9/2007 | Imoai et al. | |
| 2012/0208814 A1 | 8/2012 | Demont et al. | |
| 2015/0111885 A1 | 4/2015 | Bennett et al. | |
| 2016/0158246 A1 | 6/2016 | Bertoni et al. | |
| 2016/0200666 A1 | 7/2016 | Zhou et al. | |

FOREIGN PATENT DOCUMENTS

| | | | |
|---|---|---|---|
| CN | 105732624 A | 7/2016 | |
| CN | 105873577 A | 8/2016 | |
| JP | 2016-529246 A | 9/2016 | |
| MX | 2019/005038 A | 4/2016 | |
| WO | WO 01/51919 A2 | 7/2001 | |
| WO | WO-2012030886 A1 * | 3/2012 | ........ A61K 31/385 |
| WO | WO 2013/097601 A1 | 7/2013 | |
| WO | WO 2015/058160 A1 | 4/2015 | |
| WO | WO 2015/078929 A1 | 6/2015 | |
| WO | WO 2016/172618 A1 | 10/2016 | |
| WO | WO 2018/075796 A1 | 4/2018 | |

OTHER PUBLICATIONS

Rowe et al., Hypromellose—Related Substances, Handbook of Pharmaceutical Excipients, 2009, Sixth Edition, Pharmaceutical Press, 326-329.*
National Cancer Institute, Intraocular (Uveal) Melanoma Treatment (PDQ®)—Patient Version, National institutes of Health, Jul. 23, 2021, printed from https://www.cancer.gov/types/eye/patient/intraocular-melanoma-treatment-pdq, 17 pages.*
Thakkar et al., Glioblastoma Multiforme, American Association of Neurological Surgeons, May 5, 2021, printed from https://www.aans.org/en/Patients/Neurosurgical-Conditions-and-Treatments/Glioblastoma-Multiforme, with Google date sheet, 8 pages.*
Chau et al., Intensive treatment and survival outcomes in NUT midline carcinoma of the head and neck, Cancer, Dec. 1, 2016, 122 (23) pp. 3632-3640.*

(Continued)

*Primary Examiner* — Gigi G Huang
(74) *Attorney, Agent, or Firm* — Foley & Lardner LLP

(57) ABSTRACT

Described herein is the bromodomain inhibitor 4-[2-(cyclopropylmethoxy)-5-methylsulfonylphenyl]-2-methylisoquinolin-1-one, including crystalline forms, amorphous forms, solvates, and hydrates thereof, as well as pharmaceutical compositions that include this bromodomain inhibitor. In some embodiments, the pharmaceutical composition comprises 4-[2-(cyclopropylmethoxy)-5-methylsulfonylphenyl]-2-methylisoquinolin-1-one that has been processed by micronization or spray dried dispersion. In some embodiments, the pharmaceutical composition further comprises at least one polymer. In some embodiments, the pharmaceutical composition comprises a solid polymer matrix comprising 4-[2-(cyclopropylmethoxy)-5-methylsulfonylphenyl]-2-methylisoquinolin-1-one and at least one polymer. Pharmaceutical compositions comprising 4-[2-(cyclopropylmethoxy)-5-methylsulfonylphenyl]-2-methylisoquinolin-1-one are useful for the treatment of cancer or neoplastic disease.

15 Claims, 8 Drawing Sheets

(56) References Cited

OTHER PUBLICATIONS

Taylor, The 10 deadliest cancers, and why there's no cure, LiveScience.com, Oct. 18, 2021, printed from https://www.livescience.com/11041-10-deadliest-cancers-cure.html, 6 pages.*
UCSF Health, Fibroids Treatments, University of California San Francisco, Jan. 16, 2022, printed from https://www.ucsfhealth.org/conditions/fibroids/treatment, 8 pages.*
Expasy, Cellosaurus HL-60 (CVCL_0002), Dec. 16, 2021, printed from https://web.expasy.org/cellosaurus/CVCL_0002#top, 10 pages.*
Wesolowski et al., Temozolomide (Temodar), American Journal of Neuroradiology Sep. 2010, 31 (8) 1383-1384.*
Friesen et al., Hydroxypropyl Methylcellulose Acetate Succinate-Based Spray-Dried Dispersions: An Overview, Molecular Pharmaceutics 2008 5 (6), 1003-1019.*
Gupta et al., Methotrexate, rituximab, and temozolomide in CNS lymphoma: The Mayo Clinic experience, Journal of Clinical Oncology 2013 31:15_suppl, 2058-2058.*
Office Action issued in Mexican Patent Application No. MX/a/2017/013501, dated Feb. 26, 2020.
International Search Report and Written Opinion, dated Jun. 27, 2018, in related Singapore Application No. 11201708627T, filed Apr. 22, 2016.
Microfine—Micronization, 2012, printed from http://www.microfine.co.in/micronization.htm on Sep. 19, 2019, 2 pages.
Pubchem, Substance Record for SID 311434570, Create Date: Feb. 23, 216 [retrieved n Jun. 16, 2016]. Retrieved from the Internet, https://pubchem.ncbi.nlm.nih.gov/substance/311434570/version/1#section=Top>. Entire document.
International Preliminary Report on Patentability dated, Nov. 2, 2017, in related International Application No. PCT/US2016/029029, filed Apr. 22, 2016.
International Search Report and Written Opinion, dated, Aug. 8, 2016, in related International Application No. PCT/US2016/029029, filed Apr. 22, 2016.
Bee et al., Insolubility by spray drying, Mar. 11, 2010, printed from https://www.manufacturingchemist.com/technical/article_page/Insolubility_solved_by_spray_drying/46618.
Parikh, Achieving Pharmaceutical Solubility Enhancements Using Spray Drying, Feb. 1, 2008, printed from https://www.powderbulksolids.com/article/achieving-pharmaceutical-solubility-enhancements-using-spray-drying, 4 pages.
Winfield, Pharmaceutical Practice, Dosage forms, Churchill Livingstone, 2004, 176-180.
Gennaro et al., Remington's Pharmaceutical Sciences, Mack Pub., $21^{st}$ Edition, 2005, pp. 891-892.
International Search Report and Written Opinion, dated, Jan. 5, 2018, in related International Application No. PCT/US2017/057439, filed Oct. 19, 2017.
Office Action issued in co-pending Japanese Patent Application No. 2019-521064, dated Jul. 13, 2021.
Moribe, et al., "Preparation and Evaluation of Amorphous Medical Products," *Journal of Japanese Society* of Cryobiology and Cryotechnology, vol. 51, No. 1, pp. 19-24 (2005).
Frontiers of Oral Formulation Techniques for Poorly Water-Soluble Drugs, CMC Publishing Co., Ltd, Jul. 2016, pp. 64, 127 to 135. [partial translation].
Office Action issued in co-pending Chinese Patent Application No. 201780076154.0, dated Nov. 29, 2021.
Byrn, et al., "Pharmaceutical Solids: A Strategic Approach to Regulatory Considerations," Pharm. Research, vol. 12, No. 7, pp. 945-954 (1995).
Kawaguchi, Drug and Crystal Polymorphism, Journal of Human Environmental Engineering, vol. 4, No. 2, pp. 310-317 (2002)., [partial translation].
Yamano, "Approach to Crystal Polymorph in Process Research of New Drug," Journal of Synthetic Organic Chemistry, vol. 65, pp. 907-913 (2007). [Eng. Abstract].
Decision on Rejection issued in co-pending Japanese Patent Application No. 2019-521064, dated Dec. 14, 2021.
AquaSolve™ hydroxypropylmethylcellulose acetate succinate | Physical and chemical properties handbook, Ashland, retrieved from the internet https://manualzz.com/download/12364552 on Apr. 11, 2022, 16 pages.
Examination Report issued in co-pending Australia Patent Application No. 2017345468, dated Apr. 22, 2022.
Moreno et al., "Phase I Study of CC-90010, a reversible, oral BET Inhibitor in Patients with Advanced Solid Tumors and Relapsed/Refractory Non-Hodgkin's Lymphoma," *Annals of Oncology*, vol. 31 (6), pp. 780-788 (2020).

* cited by examiner

Temperature °C

BROMODOMAIN INHIBITOR

RELATED APPLICATIONS

This application is a divisional of U.S. patent application Ser. No. 15/788,741, filed Oct. 19, 2017, which claims priority from U.S. Provisional Patent Application No. 62/410,756, filed Oct. 20, 2016. This application is also a continuation-in-part of U.S. patent application Ser. No. 15/136,761, filed Apr. 22, 2016, which claims priority from U.S. Provisional Patent Application No. 62/151,205, filed Apr. 22, 2015, each of these applications are incorporated herein by reference in their entirety.

FIELD

The present embodiments provide compounds and pharmaceutical compositions useful for the treatment of cancer, such as, for example, 4-[2-(cyclopropylmethoxy)-5-methylsulfonyl-phenyl]-2-methylisoquinolin-1-one.

BACKGROUND

A need exists in the art for effective treatments of cancer and neoplastic disease.

SUMMARY

The present embodiments provide a bromodomain inhibitor, the compound 4-[2-(cyclopropylmethoxy)-5-methylsulfonylphenyl]-2-methylisoquinolin-1-one ("Compound 1"), which compound includes crystalline forms, amorphous forms, solvates, and hydrates thereof; as well as pharmaceutical compositions that include this compound.

At least one embodiment provides a pharmaceutical composition comprising crystalline Form A of 4-[2-(cyclopropylmethoxy)-5-methylsulfonylphenyl]-2-methylisoquinolin-1-one. In particular embodiments, the crystalline Form A of 4-[2-(cyclopropylmethoxy)-5-methyl-sulfonylphenyl]-2-methyliso-quinolin-1-one exhibits X-ray powder diffraction (XRPD) 2theta (2θ) reflection peaks at 7.8, 9.0, 15.7, 18.0, 21.1, 22.0, 23.6, and 24.5 2θ.

At least one embodiment provides a pharmaceutical composition comprising amorphous 4-[2-(cyclopropylmethoxy)-5-methylsulfonylphenyl]-2-methylisoquinolin-1-one.

In at least one embodiment, the pharmaceutical composition comprises 4-[2-(cyclopropylmethoxy)-5-methylsulfonylphenyl]-2-methylisoquinolin-1-one and at least one solid matrix polymer. A related embodiment provides a pharmaceutical composition wherein the ratio of 4-[2-(cyclopropylmethoxy)-5-methylsulfonylphenyl]-2-methylisoquinolin-1-one to solid matrix polymer is from about 1:1 to about 1:9. Another embodiment provides the pharmaceutical composition wherein the ratio of 4-[2-(cyclopropylmethoxy)-5-methylsulfonylphenyl]-2-methyl-isoquinolin-1-one to solid matrix polymer is 1:1. Another embodiment provides the pharmaceutical composition wherein the ratio of 4-[2-(cyclopropyl-methoxy)-5-methylsulfonylphenyl]-2-methyl-isoquinolin-1-one to solid matrix polymer is 1:2. Another embodiment provides the pharmaceutical composition wherein the ratio of 4-[2-(cyclopropylmethoxy)-5-methylsulfonylphenyl]-2-methyl-isoquinolin-1-one to solid matrix polymer is 1:3. Another embodiment provides the pharmaceutical composition wherein the ratio of 4-[2-(cyclopropylmethoxy)-5-methylsulfonylphenyl]-2-methyliso-quinolin-1-one to solid matrix polymer is 1:4. Another embodiment provides the pharmaceutical composition wherein the ratio of 4-[2-(cyclopropylmethoxy)-5-methylsulfonylphenyl]-2-methyliso-quinolin-1-one to solid matrix polymer is 1:5. Another embodiment provides the pharmaceutical composition wherein the ratio of 4-[2-(cyclopropylmethoxy)-5-methylsulfonylphenyl]-2-methyliso-quinolin-1-one to solid matrix polymer is 1:6. Another embodiment provides the pharmaceutical composition wherein the ratio of 4-[2-(cyclopropylmethoxy)-5-methylsulfonylphenyl]-2-methyliso-quinolin-1-one to solid matrix polymer is 1:7. Another embodiment provides the pharmaceutical composition wherein the ratio of 4-[2-(cyclopropylmethoxy)-5-methylsulfonyl-phenyl]-2-methyl-isoquinolin-1-one to solid matrix polymer is 1:8. Another embodiment provides the pharmaceutical composition wherein the ratio of 4-[2-(cyclopropylmethoxy)-5-methylsulfonylphenyl]-2-methyl-isoquinolin-1-one to solid matrix polymer is 1:9.

At least one embodiment provides a solid matrix comprising a polyvinyl-pyrrolididone derivative At least one embodiment provides a solid matrix comprising a cellulose derivative. The cellulose derivative may be at least one of hydroxypropylmethy-cellulose, hydroxypropyl-methycellulose phthalate, hydroxypropylmethylcellulose acetate stearate, or hydroxypropylmethyl-cellulose acetate succinate. Another embodiment provides the pharmaceutical composition wherein the cellulose derivative is hydroxypropylmethycellulose. Another embodiment provides the pharmaceutical composition wherein the cellulose derivative is hydroxypropylmethy-cellulose phthalate. Another embodiment provides the pharmaceutical composition wherein the cellulose derivative is hydroxypropylmethylcellulose acetate stearate. Another embodiment provides the pharmaceutical composition wherein the cellulose derivative is hydroxypropylmethylcellulose acetate succinate.

In at least one embodiment, the pharmaceutical composition comprises amorphous the 4-[2-(cyclopropylmethoxy)-5-methylsulfonylphenyl]-2-methylisoquinolin-1-one and a solid polymer matrix.

In some embodiments, the pharmaceutical composition comprises a spray dried dispersion of 4-[2-(cyclopropylmethoxy)-5-methylsulfonylphenyl]-2-methylisoquinolin-1-one, and, optionally, further comprises a solid polymer matrix. In some embodiments, the pharmaceutical composition comprises micronized 4-[2-(cyclopropylmethoxy)-5-methyl-sulfonylphenyl]-2-methylisoquinolin-1-one, and, optionally, further comprises a solid polymer matrix.

At least one embodiment provides a pharmaceutical composition comprising 4-[2-(cyclopropylmethoxy)-5-methylsulfonylphenyl]-2-methylisoquinolin-1-one, wherein the 4-[2-(cyclopropylmethoxy)-5-methylsulfonylphenyl]-2-methylisoquinolin-1-one has been prepared by a process comprising spray drying.

At least one embodiment provides a pharmaceutical composition comprising 4-[2-(cyclopropylmethoxy)-5-methylsulfonylphenyl]-2-methylisoquinolin-1-one, wherein the 4-[2-(cyclopropylmethoxy)-5-methylsulfonylphenyl]-2-methylisoquinolin-1-one has been prepared by a process comprising rapid expansion of supercritical $CO_2$ solution (RESS) micronization.

At least one embodiment provides a pharmaceutical composition comprising 4-[2-(cyclopropylmethoxy)-5-methylsulfonylphenyl]-2-methylisoquinolin-1-one and a solid matrix polymer, wherein the 4-[2-(cyclopropylmethoxy)-5-methylsulfonylphenyl]-2-methyl-isoquinolin-1-one has been processed by spray drying, and the solid matrix polymer is a polyvinyl-pyrrolididone derivative.

At least one embodiment provides a pharmaceutical composition comprising 4-[2-(cyclopropylmethoxy)-5-methylsulfonylphenyl]-2-methylisoquinolin-1-one and a solid matrix polymer, wherein the 4-[2-(cyclopropylmethoxy)-5-methylsulfonylphenyl]-2-methylisoquinolin-1-one is processed by spray drying, and the solid matrix polymer is a cellulose derivative.

At least one embodiment provides a medicament for the treatment of cancer, wherein the medicament comprises a pharmaceutical composition comprising 4-[2-(cyclopropylmethoxy)-5-methylsulfonylphenyl]-2-methylisoquinolin-1-one, wherein the pharmaceutical composition includes a spray dried dispersion of the 4-[2-(cyclopropylmethoxy)-5-methyl-sulfonylphenyl]-2-methylisoquinolin-1-one, optionally with a solid matrix polymer. At least one embodiment provides a medicament for the treatment of cancer, wherein the medicament comprises a pharmaceutical composition comprising 4-[2-(cyclopropylmeth-oxy)-5-methyl-sulfonylphenyl]-2-methyl-isoquinolin-1-one, wherein the pharmaceutical composition is prepared by a process that includes spray dried dispersion, optionally with a solid matrix polymer. The cancer may be nuclear protein in testis (NUT) midline carcinoma (NMC), prostate cancer, breast cancer, bladder cancer, lung cancer, or melanoma. The cancer may be Burkitts lymphoma. The cancer may be glioblastoma (GBM), basal cell carcinoma, pancreatic, multiple myeloma, or acute myeloid leukemia (AML).

At least one embodiment provides a method of treating cancer in a subject in need thereof, comprising administering to the subject a pharmaceutical composition comprising 4-[2-(cyclopropyl-methoxy)-5-methylsulfonylphenyl]-2-methylisoquinolin-1-one, wherein the pharmaceutical composition is prepared by a process that includes spray dried dispersion. In certain embodiments, the cancer is NMC, prostate cancer, breast cancer, bladder cancer, lung cancer, or melanoma. In another embodiment, the cancer is Burkitts lymphoma. In other embodiments, the cancer is GBM, basal cell carcinoma, pancreatic, multiple myeloma, or AML.

DETAILED DESCRIPTION

Figure 1:
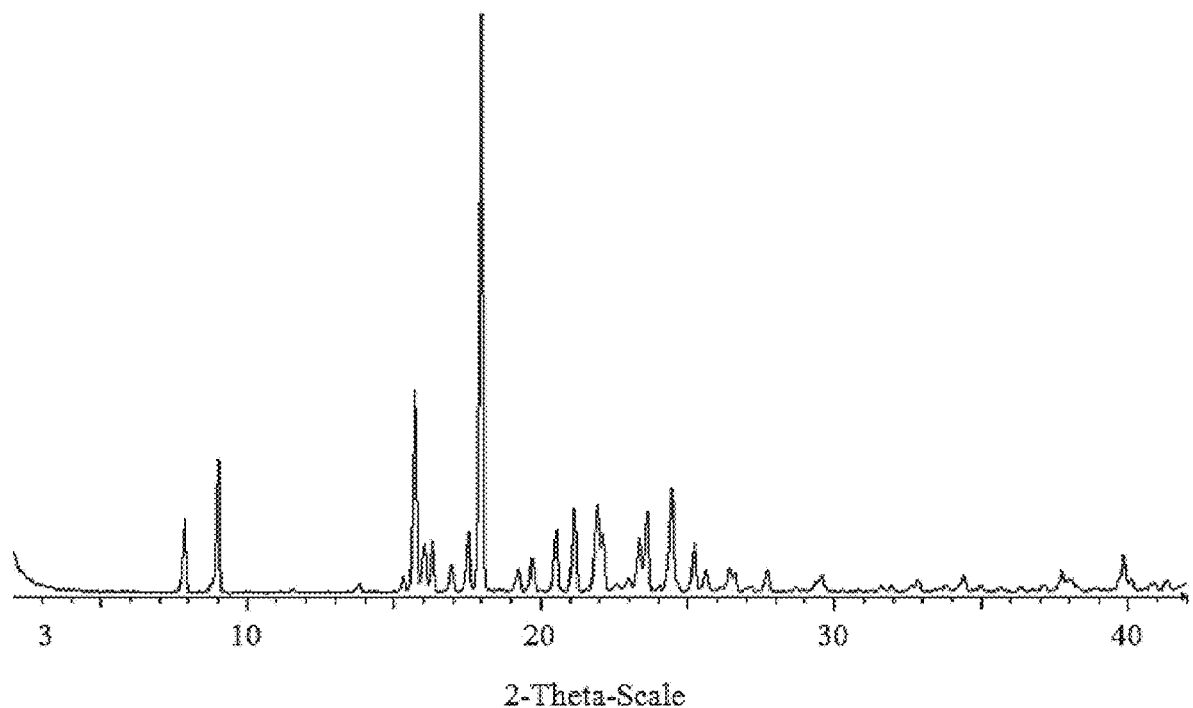
FIG. 1 shows an X-ray powder diffraction (XRPD) pattern of crystalline Form A of Compound 1.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

The bromodomain inhibitor compound described herein (i.e., Compound 1) is a bromodomain 4 (BRD4) inhibitor. In preliminary in vitro studies, BRD4 inhibition was observed, in addition to other cancer-related inhibitory activity, in several different cell lines (Raji, human Burkitts lymphoma cells; HL-60, human proleukemia cells; and NCI-H460, human non-small cell lung cancer cells). See U.S. patent application Ser. No. 14/517,705.

"Compound 1" or "4-[2-(cyclopropylmethoxy)-5-methyl-sulfonylphenyl]-2-methylisoquinolin-1-one" "the compound" or any other suitable name refers to the compound with the following structure:

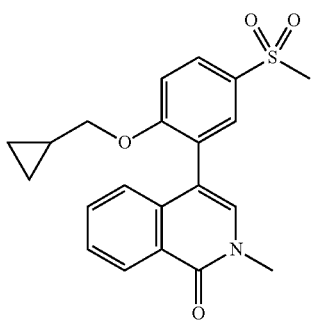 [SMILES: Cn1cc(-c2cc(S(C)(=O)=O)ccc2OCC2CC2)c2ccccc2c1=O]

In the context of the present embodiments, 4-[2-(cyclopropylmethoxy)-5-methylsulfonylphenyl]-2-methylisoquinolin-1-one or Compound 1 and the like, includes crystalline forms, amorphous forms, solvates, hydrates, and pharmaceutically acceptable salts thereof, unless the context requires specificity (e.g., "Form A"); as well as pharmaceutical compositions that include this compound. Unless otherwise stated, structures depicted herein are intended to include compounds that differ only in the presence of one or more isotopically enriched atoms or unnatural proportions of atomic isotopes at one or more atoms that constitute such compounds.

Accordingly, as described herein, Compound 1 may be prepared in various solid forms, including but not limited to, amorphous phase, crystalline forms, milled forms, micronized forms, nano-particulate forms. In some embodiments, Compound 1 is amorphous. In some embodiments, Compound 1 is amorphous and anhydrous. In some embodiments, Compound 1 is crystalline. In some embodiments, Compound 1 is crystalline and anhydrous. In some embodiments, Compound 1 is crystalline and milled. In some embodiments, Compound 1 is crystalline and in a micronized form. In some embodiments, Compound 1 is amorphous and in a micronized form. In some embodiments, Compound 1 is crystalline and in a nano-particle form. In some embodiments, Compound 1 is amorphous and dispersed with additional organic materials. In some embodiments, Compound 1 is amorphous and combined with a polymer matrix excipient. In some embodiments, Compound 1 is amorphous and processed by spray-dried dispersion.

Accordingly, as described herein, Compound 1 may be in the form of a solvate. Solvates contain either stoichiometric or non-stoichiometric amounts of a solvent, and may be formed during the process of drug substance synthesis or isolation, or drug product formulation or isolation, with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), *Impurities: Guidelines for Residual Solvents, Q3C (R5)* (February 2011). In some embodiments, solvates of Compound 1 are anhydrous. Hydrates are particular solvates formed when the solvent is water; and alcoholates are formed when the solvent is alcohol. In some embodiments, solvates of Compound 1 are hydrates. In some embodiments, Compound 1 exists in unsolvated form.

Amorphous Compound 1

Figure 2:
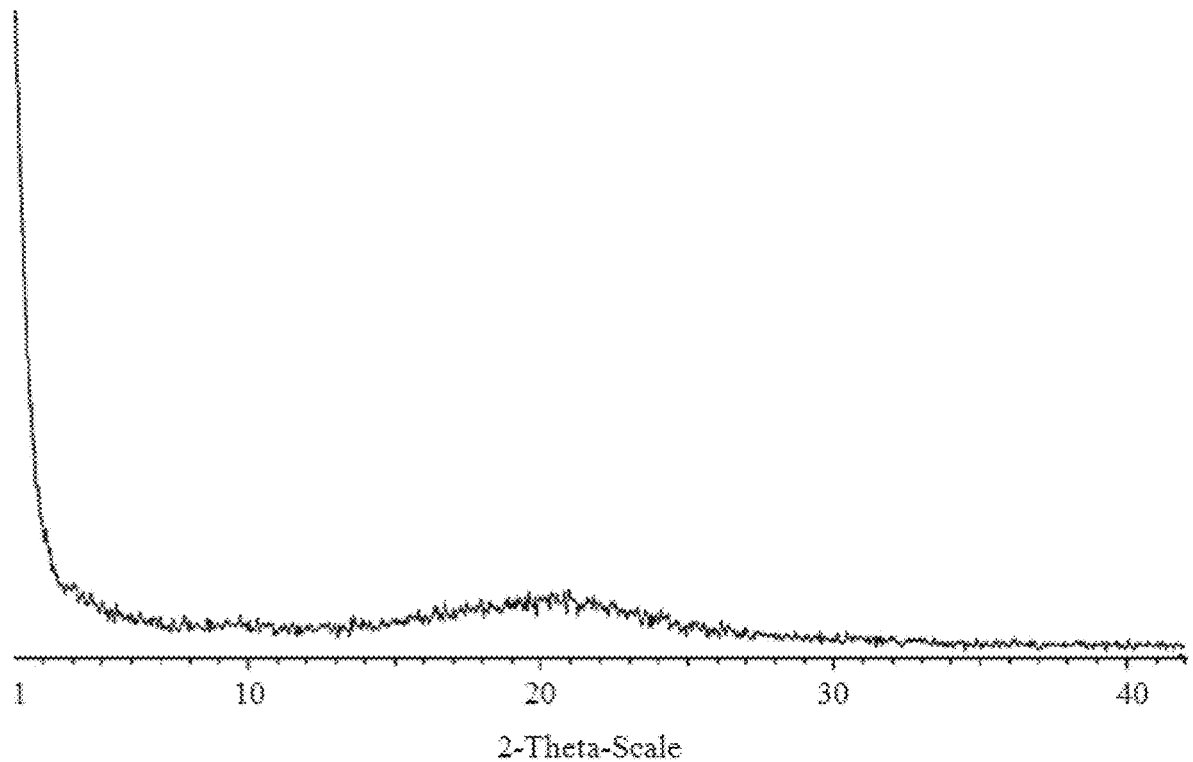
FIG. 2 shows an XRPD pattern of amorphous Compound 1.

In some embodiments, Compound 1 is amorphous. In some embodiments, amorphous Compound 1 has an X-Ray Powder Diffraction (XRPD) pattern showing a lack of crystallinity. FIG. 2 illustrates an XRPD pattern of amorphous Compound 1. One embodiment provides a pharmaceutical composition comprising amorphous 4-[2-(cyclopropylmethoxy)-5-methyl-sulfonylphenyl]-2-methylisoquinolin-1-one.

Form A Compound 1

In some embodiments, Compound 1 is crystalline. In some embodiments, Compound 1 is crystalline Form A. FIG. 1 demonstrates an XRPD pattern of crystalline Compound 1 Form A. Accordingly, some embodiments provide a pharmaceutical composition comprising crystalline form A of 4-[2-(cyclopropylmethoxy)-5-methylsulfonylphenyl]-2-methylisoquinolin-1-one.

One embodiment provides a pharmaceutical composition comprising crystalline Form A of 4-[2-(cyclopropylmethoxy)-5-methylsulfonylphenyl]-2-methylisoquinolin-1-one exhibiting at least one XRPD reflection peak selected from 7.8, 9.0, 15.7, 18.0, 21.1, 22.0, 23.6, and 24.5 2θ. One embodiment provides a pharmaceutical composition comprising crystalline Form A of 4-[2-(cyclo-propylmethoxy)-5-methylsulfonylphenyl]-2-methylisoquinolin-1-one exhibiting at least two XRPD reflection peaks selected from 7.8, 9.0, 15.7, 18.0, 21.1, 22.0, 23.6, and 24.5 2θ. One embodiment provides a pharmaceutical composition comprising crystalline form A of 4-[2-(cyclopropyl-methoxy)-5-methylsulfonylphenyl]-2-methylisoquinolin-1-one exhibiting at least three XRPD reflection peaks selected from 7.8, 9.0, 15.7, 18.0, 21.1, 22.0, 23.6, and 24.5 2θ. One embodiment provides a pharmaceutical composition comprising crystalline form A of 4-[2-(cyclopropyl-methoxy)-5-methylsulfonylphenyl]-2-methylisoquino-lin-1-one exhibiting at least four XRPD reflection peaks selected from 7.8, 9.0, 15.7, 18.0, 21.1, 22.0, 23.6, and 24.5 2θ. One embodiment provides a pharmaceutical composition comprising crystalline form A of 4-[2-(cyclopropyl-methoxy)-5-methylsulfonylphenyl]-2-methylisoquinolin-1-one exhibiting XRPD reflection peaks at 7.8, 9.0, 15.7, 18.0, 21.1, 22.0, 23.6, and 24.5 2θ. One embodiment provides a pharmaceutical composition comprising crystalline Form A of 4-[2-(cyclopropylmethoxy)-5-methylsulfonyl-phenyl]-2-methylisoquino-lin-1-one exhibiting the XRPD pattern of FIG. 1.

Preparation of Crystalline Forms

In some embodiments, crystalline forms of 4-[2-(cyclopropylmethoxy)-5-methyl-sulfonylphenyl]-2-methylisoquinolin-1-one are prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), *Impurities: Guidelines for Residual Solvents*, Q3C(R5), (February 2011).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Examples of Class 1 solvents, for which measurable amounts thereof are avoided in drug products, include benzene, carbon tetrachloride, 1,2-dichloroethane, 1,1-dichloroethene, and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Examples of Class 3 solvents, which possess low toxicity, include acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process. The amount of residual solvent carried over from API to finished drug product may also be considered.

In some embodiments, compositions comprising Compound 1 include an organic solvent(s). In some embodiments, compositions comprising Compound 1 comprise a residual amount or trace amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

Certain Terminology

The term "acceptable" or "pharmaceutically acceptable", with respect to a pharmaceutical composition, formulation, or ingredient, means having no persistent detrimental effect on the general health of the subject being treated, does not abrogate the biological activity or properties of the compound, and is considered relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of API (e.g., Compound 1) in a dose that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which API (e.g., Compound 1) is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments, the presence of a modulator results in an activity that does not occur in the absence of the modulator.

"Optional" or "optionally" means that a described event or circumstance may or may not occur and that the description includes instances when the event or circumstance occurs and instances in which it does not.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Pharmaceutically acceptable salts of the Compound 1 are pharmaceutically acceptable acid addition salts and pharmaceutically acceptable base addition salts.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" as used herein, refers to an animal which is the object of treatment, observation, or experiment. By way of example only, a subject may be, but is not limited to, an animal, such as a mammal, including a human or non-human primate. The terms patient and subject may be used interchangeably.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients understood as pharmaceutically acceptable may be used as suitable and as understood in the art. Pharmaceutically acceptable excipients and formulations are known in the art. See, e.g., REMINGTON: SCIENCE & PRACTICE OF PHARMACY, 19th Ed. (Mack Publishing Co., Easton, Pa., 1995); PHARMACEUTICAL DOSAGE FORMS (Liberman & Lachman, eds., Marcel Decker, New York, N.Y., 1980); PHARMACEUTICAL DOSAGE FORMS & DRUG DELIVERY SYSTEMS, 7th Ed. (Lippincott Williams & Wilkins, 1999).

A pharmaceutical composition or pharmaceutical formulation, as used herein, refers to a mixture of Compound 1 with other excipients, e.g., carriers, stabilizers, diluents, dispersing agents, suspending agents, thickening agents, or means for sustained or control release. A pharmaceutical composition may facilitate administration of the Compound 1 to a subject, such as a mammal. In practicing the methods of treatment or use provided herein, therapeutically effective amounts of Compound 1 are generally administered in a pharmaceutical composition to a subject having a disease, disorder, or condition to be treated. The subject may be a mammal, such as a human. A therapeutically effective amount can vary widely depending on the severity of the disease, the age and relative health of the subject, the potency of the compound used, and other factors. Compound 1 may be used singly or in combination with one or more therapeutic agents as components of mixtures. Compound 1 may be used as a sole therapeutic treatment, or in combination with one or more therapeutic agents or treatment modalities in the treatment of the disease condition.

In some embodiments, pharmaceutical compositions comprising crystalline Compound 1 are formulated for solid oral administration. In other embodiments, pharmaceutical compositions comprising crystalline Compound 1 are formulated for other-than-oral administration. The pharmaceutical compositions described herein include, but are not limited to, aqueous liquid dispersions, self-emulsifying dispersions, solid solutions, liposomal dispersions, aerosols, solid dosage forms, powders, tablets, capsules, pills, immediate release formulations, fast melt formulations, sustained release formulations, controlled release formulations, delayed release formulations, extended release formulations, pulsatile release formulations, multiparticulate formulations, or formulations comprising mixed immediate and controlled release forms. Accordingly, the pharmaceutical compositions described herein can be administered to a subject by multiple administration routes, including but not limited to, oral, parenteral (e.g., intravenous, subcutaneous, intramuscular), intranasal, buccal, topical, rectal, or transdermal administration routes.

Pharmaceutical compositions including Compound 1 may be manufactured in a conventional manner, such as, by way of example only, by means of conventional mixing, micronization, spray dry dispersion, nanoparticle formation, dissolving, granulating, dragee-making, levigating, emulsifying, encapsulating, entrapping, or compression processes.

The pharmaceutical compositions described herein can be formulated for administration to a subject (e.g., mammal) via any conventional means including, but not limited to, oral, parenteral (e.g., intravenous, subcutaneous, or intramuscular), buccal, intranasal, rectal or transdermal administration routes.

Accordingly, one embodiment provides a pharmaceutical composition comprising 4-[2-(cyclopropylmethoxy)-5-methylsulfonylphenyl]-2-methylisoquinolin-1-one, wherein the 4-[2-(cyclopropylmethoxy)-5-methylsulfonylphenyl]-2-methylisoquinolin-1-one is processed by spray drying, and the solid matrix polymer is a polyvinylpyrrolididone derivative.

One embodiment provides a pharmaceutical composition comprising 4-[2-(cyclo-propylmethoxy)-5-methylsulfonylphenyl]-2-methylisoquinolin-1-one, wherein the 4-[2-(cyclo-propylmethoxy)-5-methylsulfonylphenyl]-2-methylisoquinolin-1-one is processed by spray drying and the solid matrix polymer is a cellulose derivative.

Another embodiment provides the pharmaceutical composition wherein the ratio of 4-[2-(cyclopropylmethoxy)-5-methylsulfonylphenyl]-2-methylisoquinolin-1-one to solid matrix polymer is from about 1:1 to about 1:9. Another embodiment provides the pharmaceutical composition wherein the ratio of 4-[2-(cyclopropylmethoxy)-5-methylsulfonylphenyl]-2-methyl-isoquinolin-1-one to solid matrix polymer is 1:1. Another embodiment provides the pharmaceutical composition wherein the ratio of 4-[2-(cyclopropylmethoxy)-5-methyl-sulfonylphenyl]-2-methyl-isoquinolin-1-one to solid matrix polymer is 1:2. Another embodiment provides the pharmaceutical composition wherein the ratio of 4-[2-(cyclopropyl-methoxy)-5-methylsulfonylphenyl]-2-methyl-isoquinolin-1-one to solid matrix polymer is 1:3. Another embodiment provides the pharmaceutical composition wherein the ratio of 4-[2-(cyclopropyl-methoxy)-5-methylsulfonylphenyl]-2-methyl-isoquinolin-1-one to solid matrix polymer is 1:4. Another embodiment provides the pharmaceutical composition wherein the ratio of 4-[2-(cyclo-propylmethoxy)-5-methylsulfonylphenyl]-2-methylisoquinolin-1-one to solid matrix polymer is 1:5. Another embodiment provides the pharmaceutical composition wherein the ratio of 4-[2-(cyclopropylmethoxy)-5-methylsulfonyl-phenyl]-2-methylisoquinolin-1-one to solid matrix polymer is 1:6. Another embodiment provides the pharmaceutical composition wherein the ratio of 4-[2-(cyclopropylmethoxy)-5-methylsulfonyl-phenyl]-2-methylisoquinolin-1-one to solid matrix polymer is 1:7. Another embodiment provides the pharmaceutical composition wherein the ratio of 4-[2-(cyclopropylmethoxy)-5-methylsulfonyl-phenyl]-2-methylisoquinolin-1-one to solid matrix polymer is 1:8. Another embodiment provides the pharmaceutical composition wherein the ratio of 4-[2-(cyclopropylmethoxy)-5-methylsulfonyl-phenyl]-2-methylisoquinolin-1-one to solid matrix polymer is 1:9.

Another embodiment provides the pharmaceutical composition wherein the cellulose derivative is hydroxypropylmethycellulose. Another embodiment provides the pharmaceutical composition wherein the cellulose derivative is hydroxypropylmethycellulose phthalate. Another embodiment provides the pharmaceutical composition wherein the cellulose derivative is hydroxypropylmethylcellulose acetate stearate. Another embodiment provides the pharmaceutical composition wherein the cellulose derivative is hydroxypropylmethylcellulose acetate succinate. Another embodiment provides the pharmaceutical composition wherein the 4-[2-(cyclopropyl-methoxy)-5-methylsulfonylphenyl]-2-methylisoquinolin-1-one is amorphous and the composition is prepared by SDD.

Dosage Forms

The pharmaceutical compositions described herein, which include Compound 1, can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Dosage forms for oral use can be obtained by mixing at least one suitable solid excipient with at least Compound 1, optionally grinding the resulting mixture to form granules, and processing the mixture of granules, optionally after adding suitable auxiliaries, to obtain tablets or dragee cores. Suitable excipients include, for example, pharmaceutically acceptable fillers such as sugars, including lactose, sucrose, mannitol, or sorbitol; cellulosic preparations such as, maize starch, wheat starch, rice starch, potato starch, gelatin, gum tragacanth, methylcellulose, microcrystalline cellulose, hydroxypropylmethylcellulose, sodium carboxy-methylcellulose; or other excipients such as polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations for oral use also include push-fit capsules made of gelatin, as well as soft, sealed capsules made of gelatin and a plasticizer, such as glycerol or sorbitol. The push-fit capsules can contain the active ingredients, i.e., Compound 1, in admixture with excipients such as fillers, e.g., lactose; binders such as starches; or lubricants such as talc or magnesium stearate; and, optionally, stabilizers. In soft capsules, the active compound(s) may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, solid dosage forms disclosed herein may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), a solid dispersion, a solid solution, a bioerodible dosage form, sustained release dosage form, controlled release dosage form, pulsatile release dosage form, multi-particulate dosage form, or pellets or granules, or may be in the form of an aerosol. In other embodiments, the dosage form is a powder. In still other embodiments, the dosage form is in the form of a tablet, including but not limited to, a fast-melt tablet. Additionally, dosage forms described herein may be administered as a single capsule or in multiple capsule dosage form. In some embodiments, the dosage form is administered in two, or three, or four, capsules or tablets.

In some embodiments, solid dosage forms, e.g., tablets, effervescent tablets, and capsules, are prepared by mixing particles of Compound 1 with at least one pharmaceutical excipient to form a bulk blend composition. When referring to these bulk blend compositions as homogeneous, it is meant that the particles of Compound 1 are dispersed evenly throughout the composition so that the composition may be readily subdivided into equally effective unit dosage forms, such as tablets, pills, and capsules. The individual unit dosage formss may also include film coatings, which disintegrate upon oral ingestion or upon contact with diluent. These dosage forms can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., Theory & Practice of Indus. Pharm. (Lea & Febiger, 1986). Other methods include, e.g., spray drying, pan coating, melt granulation, granulation, fluidized bed spray drying or coating (e.g., wurster coating), tangential coating, top spraying, tableting, extruding and the like.

Drug absorption is a complex process driven by many physicochemical factors. For example, particle size may play a major role in absorption of slowly dissolving drugs. The dissolution rate of solid particles is often proportional to surface area, and surface area is directly related to particle size. Dosage forms for oral use can be obtained by milling or other physical means to reduce particle size of API, excipients, or mixtures thereof. Micronization is the process of reducing the diameter of a solid material's particle size. In at least one embodiment, Compound 1 is micronized. In some embodiments, micronized Compound 1 is obtained by physical means such as milling or grinding. In other embodiments, micronized Compound 1 is micronized via the Rapid Expansion of the Supercritical $CO_2$ Solution (RESS) process. In some embodiments, the micronized Compound 1 has a particle size distribution from about 200 nm to about 600 nm, from about 600 nm to about 1,000 nm, from about 1,000 nm to about 1,400 nm, or from about 1400 nm to about 1,800 nm. In some embodiments, the micronized Compound 1 is crystalline Form A. In some embodiments, the micronized Compound 1 is amorphous.

At least one embodiment provides a pharmaceutical composition comprising 4-[2-(cyclopropylmethoxy)-5-methylsulfonylphenyl]-2-methylisoquinolin-1-one, wherein the 4-[2-(cyclopropylmethoxy)-5-methylsulfonylphenyl]-2-methylisoquinolin-1-one is processed by spray drying.

One embodiment provides a pharmaceutical composition comprising 4-[2-(cyclo-propylmethoxy)-5-methylsulfonylphenyl]-2-methylisoquinolin-1-one, wherein the 4-[2-(cyclo-propylmethoxy)-5-methylsulfonylphenyl]-2-methylisoquinolin-1-one is micronized by the RESS process.

Dosage forms for oral use can also be obtained by use of spray drying, melt extrusion, or thermo-kinetic mixing technology. Typically, the material resulting from the use of spray dry technology is a dispersion of amorphous API within a solid matrix. The resulting solid dispersions exhibit increased drug surface area, reduced drug crystallinity, and may offer increased stability of the API during storage. The solid matrix is typically a water soluble or water miscible organic or inorganic polymer.

Suitable matrix polymers include those derived from sugars such as lactose, glucose, sucrose (e.g., Dipac®), dextrose, dextrin, molasses, mannitol, sorbitol, xylitol (e.g., Xylitab®), polysaccharide acids, microcrystalline dextrose, amylose; cellulose preparations such as starch, maize starch, wheat starch, rice starch, pregelatinized starch potato starch, micro-crystalline cellulose (e.g., Avicel®), larch araboga-lactan; proteins such as gelatin; natural or synthetic gum such as acacia, ghatti gum, mucilage of isapol husks, gum tragacanth; organic polymers such as methyl-cellulose, microcrystalline cellulose, croscarmellose, sodium croscarmellose, hydroxypropylmethyl-cellulose, sodium carboxymethylcellulose, hydroxyethylcellulose, hydroxypropylcellulose (e.g., Klucel®), ethylcellulose (e.g., Ethocel®), hydroxypropylmethycellulose (HPMC), hydroxypropylmethy-cellulose phthalate, hydroxypropylmethyl-cellulose acetate stearate (HPMCAS), cross-linked carboxymethylcellulose, methylcellulose (e.g., Methocel®), hydroxypropyl methylcellulose (e.g., Hypromellose or PharmacoatO), hydroxypropylmethylcellulose acetate stearate (HS-LF and HS), hydroxypropylmethylcellulose acetate succinate (AquaSolve®, HPMC-AS), HPMCAS-L, HMPCAS-M, HPMCAS-H; synthetic polymers such as polyvinyl acetate (PVA), polyvinyl acetate phthalate (PVAP), crospovidone (cross linked polyvinyl N-pyrrolidone), polyvinylpyrrolidone/vinyl acetate copolymer, poly-vinylpyrrolidone (PVP, e.g., Povidone® CL, Kollidon® CL, Polyplasdone® XL-10, Povidone® K-12), polyethylene glycol; or clays such as magnesium aluminum silicate (e.g., Veegum®) or bentonite (absorbent aluminium phyllosilicate clay).

Process steps such as feed solution preparation, feed solution atomization, and spray drier inlet and outlet temperatures, are optimized as is well known in the art. See. e.g., Remington's Pharm. Sci., 20th Ed. (2000). In some embodiments, the pharmaceutical solid dosage forms described herein include Compound 1 that has been processed by spray drying. In some embodiments, the dosage form described herein comprises is a solid matrix comprising Compound 1 that has been incorporated into the solid matrix via spray dried dispersion.

The pharmaceutical solid dosage forms described herein can include Compound 1 and at least one pharmaceutically acceptable additive such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures (such as those described in, e.g., Remington's, 2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are neither microencapsulated nor coated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, mono-glyceride, diglyceride, pregelatinized starch, hydroxypropylmethylcellulose, hydroxypropylmethyl-cellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropyl-methycellulose phthalate, hydroxypropylmethylcellulose acetate stearate (HPMCAS), sucrose, xylitol, lactitol, mannitol, sorbitol, sodium chloride, polyethylene glycol, and the like.

In order to release API from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations. For example, in powder filled capsule formulations binders aid in the formation of plugs that can be filled into soft or hard shell capsules; and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropyl-methylcellulose (e.g. Hypromellose USP Pharmacoat-603, hydroxypropylmethylcellulose acetate stearate (Agoate HS-LF and HS), hydroxypropylmethylcellulose acetate succinate (HPMC-AS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinyl-pyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20% to 70% can be used in powder-filled gelatin capsule formulations. Binder usage levels in tablet formulations vary depending on the application of direct compression, wet granulation, roller compaction, or usage of other excipients such as fillers that may act as moderate binders. Formulators skilled in art can determine the binder level for the formulation, but binder levels of up to 70% in tablet formulations are common.

Suitable lubricants or glidants for use in the solid dosage forms described herein may include stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypoly-ethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumerate, stearic acid, sodium stearates, magnesium stearate, zinc stearate, and waxes. In some embodiments, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non-water-soluble diluent" represents compounds typically used in the formulation of pharmaceutical compostions and dosage forms, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinyl-pyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethyl-cellulose, polysorbate-80, hydroxy-ethylcellulose, hydroxypropylmethylcellulose-acetate-succinate (HPMCAS), sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxy-methylcellulose, hydroxypropyl-methylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, butylated hydroxytoluene (BHT), sodium ascorbate, tocopherols, or tocotrienols.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, poly-ethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets that are designed to dissolve in the mouth include one or more flavoring agents. In other embodiments, the compressed tablets include a film surrounding the final compressed tablet (i.e., a film coating). In some embodiments, the film coating can provide a delayed release of Compound 1 from the formulation. In other embodiments, the film coating aids in patient compliance (e.g., Opadry® coatings or sugar coating for easing oral administration). Film coatings including Opadry® typically range from about 1% to about 3% of the tablet weight. As noted, in some embodiments compressed tablets include one or more additional excipients.

A capsule may be prepared, for example, by placing the bulk blend of the formulation of Compound 1 inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates in a predetermined time frame after oral administration, thereby releasing the formulation into the gastrointestinal fluid: such as in less than about 30 minutes, less than about 35 minutes, less than about 40 minutes, less than about 45 minutes, less than about 50 minutes, less than about 55 minutes, or less than about 60 minutes.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents. Materials useful for the microencapsulation include materials compatible with Compound 1, which sufficiently isolate Compound 1 from other non-compatible excipients or components of the formulation.

Materials compatible with Compound 1 microencapsulation may include those that delay the in vivo release of Compound 1. Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethyl-cellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethyl-celluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel™ hydroxypropylcellulose. In still other embodiments, the microencapsulation material is Methocel™ cellulose ether.

Microencapsulated Compound 1 may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1are microencapsulated prior to being formulated into one of the above forms. In still another embodiment, some or most of the particles are coated prior to being further formulated by using standard coating procedures, such as those described in REMINGTON'S, 2000).

In other embodiments, the solid dosage formulations of the Compound 1 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In some embodiments, pharmaceutical formulations are provided that include particles of Compound 1and at least one dispersing agent or suspending agent for oral administration to a subject. The formulations may be a powder or granules for suspension, and upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Bromodomain Inhibition

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell, where the chromosomes exist in a complex of nucleic acids and proteins called chromatin. Histones are the chief protein components of chromatin. There are a total of six classes of histones (H1, H2A, H2B, H3, H4, and H5) organized into two classes: core histones (H2A, H2B, H3, and H4) and linker histones (H1 and H5). The basic unit of chromatin is a nucleosome, which comprises about 147 base pairs of DNA wrapped around a core histone octamer which includes two copies each of the core histones: H2A, H2B, H3, and H4. These nucleosome units are then further organized and condensed by the aggregation and folding of nucleosomes to form the highly condensed chromatin structure. A range of different states of condensation are possible, and the tightness of chromatin structure varies during the cell cycle, being most compact during the process of cell division.

Accordingly, chromatin structure plays a critical role in regulating gene transcription, which cannot occur efficiently in highly condensed chromatin. Chromatin structure is controlled by a series of post translational modifications to histone proteins, notably to histones H3 and H4, and most commonly within the "histone tails" which extend beyond the core nucleosome structure. These post translational modifications include acetylation, methylation, phosphorylation, ribosylation sumoylation, ubiquitination, citrullination, deimination, and biotinylation. In addition to the histone tails, the cores of histones H2A and H3 can be modified. Given the function of histones in chromatin, histone modifications are integral to diverse biological processes such as gene expression, DNA replication, DNA repair, and chromosome condensation.

Histone Acetylation and Bromodomains

Histone acetylation is generally associated with the activation of gene transcription, as the modification is known to loosen the interaction of the DNA and the histone octamer by changing the electrostatic state. In addition to this physical change, specific proteins are known to bind to acetylated lysine residues within histones in order to function according to the epigenetic code. Bromodomains are small (~110 amino acids) distinct domains within proteins that commonly, but not exclusively, bind to acetylated lysine residues in the context of histones. Approximately fifty proteins are known to contain bromodomains, and they have a range of functions within the cell.

The BET family of bromodomain containing proteins comprises four proteins (BRD2, BRD3, BRD4, and BRD-t) which contain tandem bromodomains capable of binding to two acetylated lysine residues that are positioned in close proximity, increasing the specificity of the interaction. Bromodomain-containing proteins that recognize acetylated lysines on histones (such as BET proteins and non-BET proteins) have been implicated in proliferative disease. For example, homozygous BRD4 knockout mice are compromised in their ability to maintain an inner cell mass and die shortly after embryo implantation, and heterozygote BRD4 knockouts display pre- and postnatal growth defects associated with reduced proliferation rates. BRD4 regulates genes expressed during M/G1, including growth-associated genes, and remains bound to chromatin throughout the cell cycle. Dey, et al., 20 Mol. Biol. Cell 4899 (2009). BRD4 also associates physically with Mediator and P-TEFb (a heterodimer of Cyclin-dependent kinase 9 [CDK9], cyclin K, cyclin T, or cyclin T2a or T2b) to facilitate transcriptional elongation. Yang et al., 24 Oncogene 1653 (2005); Yang et al., 19

Mol. Cell 535 (2005). CDK9 is linked to c-Myc-dependent transcription, and is thus a validated target in chronic lymphocytic leukemia (CLL). Phelps et al., 113 Blood 2637 (2009); Rahl et al., 141 Cell 432 (2010).

Moreover, BRD4 is translocated to the nuclear protein in testis (NUT protein) in patients with lethal midline carcinoma, an aggressive form of human squamous carcinoma. French et al., 159 Am. J. Pathol. 1987 (2001). In vitro analysis with RNAi supports a causal role for BRD4 in a recurrent chromosomal translocation, t(15;19)(q13;p13.1), which defines a lethal midline carcinoma. French et al., 63 Cancer Res. 304 (2003). Also, inhibition of the BRD4 bromodomains has been found to result in growth arrest/differentiation of BRD4-NUT cell lines in vitro and in vivo. Filippakopoulos et al., *Selective Inhibition of BET Bromodomains*, 468 Nature 1067 (2010).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression. Hargreaves et al., 138 Cell 129 (2009); LeRoy et al., 30 Molec. Cell 51 (2008); Jang et al., 19 Molec. Cell 523 (2005); Yang et al., 19 Molec. Cell 535 (2005). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo. Nicodeme et al., *Suppression of Inflammation by a Synthetic Histone Mimic*, 468 Nature 1119 (2010).

Bromodomain-containing proteins (such as BET proteins) have also been found to play a role in viral infection. For example, BRD4 is implicated in the primary and persistent phases of human papilloma virus (HPV) infection of basal epithelia, in which BRD4 binding maintains the viral genome as an extra-chromosomal episome. In some strains of HPV, BRD4 binding to the HPV transcriptional activator protein, E2 (early protein 2), tethers the viral genome to infected-cell chromosomes. BRD4-E2 binding is crucial for both transactivating E2 and repressing transcription of two HPV oncoproteins (early protein 6 [E6] and early protein 7 [E7]). Disruption of BRD4 or the BRD4-E2 interaction blocks E2-dependent gene activation. BRD4 also functions to tether other classes of viral genomes (e.g., Herpes virus, Epstein-Barr virus) to the chromatin of infected cells. Kurg, in DNA REPLICATION—CURRENT ADVANCES 613 (Seligmann, ed., InTech, Rijeka, Croatia, 2011).

Bromodomain-containing proteins has also been found to bind to acetylated lysine residues on proteins other than histones. For example, the bromodomain of CREB binding protein transcriptional coactivator (CBP) allows for recognition of p53 with acetylated Lys382. The interaction between the bromodomain and acetyl-p53 follows DNA damage and promotes p53-induced transcriptional activation of the CDK inhibitor p21 and cell cycle arrest.

Another novel bromodomain-containing protein is BAZ2B, whose biological function, is believed to function similarly to ACF1, the *Drosophila* BAZ2B ortholog. ACF complexes play roles in establishing regular nucleosome spacing during chromatin assembly and influencing different remodeling outcomes at target loci.

One embodiment provides a method of regulating gene transcription in a cell comprising contacting a bromodomain-containing protein with a compound of Compound 1. Another embodiment provides a method of inhibiting bromodomain-mediated recognition of an acetyl lysine region of a protein comprising contacting the bromodomain with a compound of Compound 1.

Medicaments and Methods of Treatment

The compositions described herein are generally useful for the inhibition of activity of one or more proteins involved in epigenetic regulation. Thus, at least one embodiment provides a method of modulating epigenetic regulation mediated by one or more proteins containing acetyl-lysine recognition motifs, also known as bromodomains (e.g., BET proteins, such as BRD2, BRD3, BRD4, or BRDT, and non-BET proteins, such as CBP, ATAD2A, GCN5L, BAZ2B, FALZ, TAF1, or BRPF1) or a mutant thereof, by contacting a cell, or chomatin within a cell, with Compound 1. At least one embodiment provides a method of modulating epigenetic regulation mediated by one or more proteins containing acetyl-lysine recognition motifs, also known as bromodomains (e.g., BET proteins, such as BRD2, BRD3, BRD4, or BRDT, and non-BET proteins, such as CBP, ATAD2A, GCN5L, BAZ2B, FALZ, TAF1, or BRPF1), or a mutant thereof, by administering to a subject a pharmaceutical composition comprising Compound 1. In some embodiments, the bromodomain-containing protein is a BET protein. In some embodiments, the BET protein is BRD4.

Some embodiments provide a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1) or a mutant thereof, by contacting a cell, or chomatin within a cell, with Compound 1. Some embodiments provide a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1), or a mutant thereof, in a subject, comprising the step of administering to the subject a pharmaceutical composition comprising Compound 1. In some embodiments, the bromodomain-containing protein is a BET protein. In some embodiments, the BET protein is BRD4.

In some embodiments is provided a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1) or a mutant thereof, in a biological sample comprising the step of contacting said biological sample with Compound 1. In some embodiments, the bromodomain-containing protein is a BET protein. In some embodiments, the BET protein is BRD4.

Diseases and conditions treatable according to the methods of this invention include cancer, neoplastic disease, and other proliferative disorders. Thus, one aspect is a method of treating a subject having cancer, a neoplastic disease and other proliferative disorder, the method comprising administration of a pharmaceutical composition comprising Compound 1 to the subject. In one embodiment, a human patient is treated with a pharmaceutical composition comprising Compound 1 as described herein, wherein Compound 1 is present in an amount effective to measurably inhibit bromodomain-containing protein activity (such as BRD2, BRD3, BRD4, or BRDT) in the subject.

The invention further provides a method of treating a subject, such as a human, suffering from cancer, a neoplastic disease, or other proliferative disorder. The method comprises administering to a subject in need of such treatment a therapeutically effective amount of a pharmaceutical composition comprising Compound 1 as described herein, which functions by inhibiting a bromodomain (e.g., BRD4) and, in general, by modulating gene expression, thus inducing various cellular effects, in particular induction or repression of gene expression, arresting cell proliferation, inducing cell differentiation, or inducing apoptosis.

The invention further relates to a method for treating or ameliorating cancer, neoplastic disease, or another proliferative disorder by administration of an effective amount of a pharmaceutical composition comprising Compound 1 as described herein, to a mammal, in particular a human, in need of such treatment. In some aspects of the invention, the disease to be treated by the methods of the present invention is cancer.

One embodiment provides a method of treating cancer in a patient in need thereof, comprising administering to the patient a pharmaceutical composition comprising 4-[2-(cyclo-propylmethoxy)-5-methylsulfonylphenyl]-2-methylisoquinolin-1-one, wherein the pharmaceutical composition is prepared by a process that includes spray dried dispersion.

At least one embodiment provides a medicament for treating a cancer, neoplastic disease, or other proliferative disorder wherein the medicament comprises Compound 1 as described herein. The medicament may comprise a pharmaceutical composition comprising Compound 1 and a polymer matrix. The medicament may comprise a pharmaceutical composition in which Compound 1 is amorphous Compound 1 or Form A Compound 1. The medicament may comprise a pharmaceutical composition in which Compound 1 is micronized.

In some embodiments, the cancer treated by a medicament comprising Compound 1 is NUT midline carcinoma, prostate cancer, breast cancer, bladder cancer, lung cancer, or melanoma. In some embodiments, the cancer is Burkitts lymphoma. In some embodiments, the cancer is gliobastoma (GBM), basal cell carcinoma, pancreatic carcinoma, multiple myeloma, or acute myeloid leukemia (AML).

EXAMPLES

The following ingredients, formulations, processes and procedures for practicing the methods disclosed herein correspond to that described above. Other embodiments and uses will be apparent to one skilled in the art in light of the present disclosures. The following examples are provided merely as illustrative of various embodiments and shall not be construed to limit the invention in any way.

Example 1: Synthesis of 4-[2-(cyclopropyl-methoxy)-5-methylsulfonylphenyl]-2-methylisoquinolin-1-one (Compound 1)

Unless otherwise noted, reagents and solvents were used as received from commercial suppliers, such as Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatises detail the synthesis of reactants useful in the preparation of compounds described herein, or provide references to articles that describe the preparation. See, e.g., SYNTHETIC ORGANIC CHEM. (John Wiley & Sons, Inc., NY); Sandler et al., ORGANIC FUNCTIONAL GROUP PREPARATIONS (2nd Ed., Acad. Press, NY, 1983); House, MODERN SYNTHETIC REACTIONS (2nd Ed., W.A. Benjamin, Inc., Menlo Park, Calif., 1972); Gilchrist, HETEROCYCLIC CHEM. (2nd Ed., John Wiley & Sons, N Y, 1992) March, ADV. ORGANIC CHEM.: REACTIONS, MECH. & STRUCTURE (4th Ed., Wiley-Intersci., NY, 1992). Additional suitable reference books and treatises detail the synthesis of reactants useful in the preparation of compounds described herein, or provide references to articles that describe such preparations. See, e.g., Fuhrhop & Penzlin, ORGANIC SYNTHESIS: CONCEPTS, METHODS, STARTING MATERIALS: SECOND, REVISED & ENLARGED ED. (John Wiley & Sons ISBN: 3-527-29074-5, 1994); Hoffman, ORGANIC CHEM., AN INTERMEDIATE TEXT (Oxford Univ. Press, ISBN 0-19-509618-5, 1996); Larock, COMPREHENSIVE ORGANIC TRANSFORMATIONS: GUIDE TO FUNCTIONAL GROUP PREPARATIONS (2nd Ed., Wiley-VCH, ISBN: 0-471-19031-4, 1999); Otera (Ed.), MODERN CARBONYL CHEM. (Wiley-VCH, ISBN: 3-527-29871-1, 2000); Patai, PATAI'S 1992 GUIDE TO THE CHEM. OF FUNCTIONAL GROUPS (Intersci. ISBN: 0-471-93022-9, 1992); Solomons, ORGANIC CHEM. (7th Ed., John Wiley & Sons, ISBN: 0-471-19095-0, 2000); Stowell, INTERMEDIATE ORGANIC CHEM. (2nd Ed. Wiley-Intersci., ISBN: 0-471-57456-2, 1993); INDUS. ORGANIC CHEM.: STARTING MATS. & INTERMEDIATES: AN ULLMANN'S ENCYCLO. (John Wiley & Sons, ISBN: 3-527-29645-X, 1999), in 8 vols.; ORGANIC REACTIONS (John Wiley & Sons, 1942-2000), in over 55 volumes; CHEM. OF FUNCTIONAL GROUPS (John Wiley & Sons), in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., can be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is Stahl & Wermuth, HANDBOOK OF PHARMACEUTICAL SALTS (Verlag Helvetica Chimica Acta, Zurich, 2002).

General methods for the synthesis of substituted heterocyclic derivatives are provided in, but not limited to, the following references: WO 2009/158396; WO 2005/63768; WO 2006/112666; Briet et. al., 58 Tetrahedron 5761 (2002); WO 2008/77550; WO 2008/77551; WO 2008/77556; WO 2007/12421; WO 2007/12422; US 2007/99911; WO 2008/77550; Havera et al., 42 J. Med. Chem. 3860 (1999); WO 2004/29051; and US 2009/0054434. Additional examples of the synthesis of substituted heterocyclic derivatives are found in the following references: WO 2012/171337, WO 2011/044157; WO 2009/097567; WO 2005/030791; EP 203216; Becknell et al., 21 Bioorg. & Med. Chem. Letters 7076 (2011); Svechkarev et al., 770 Bich Bıchик

Харківського національного університету імені
В.Н.Каразіна 201 (2007); Coskun et al., 35 Synth.
Commc'ns 2435 (2005); Alvarez et al., 15 Sci. Synth. 839
(2005); Kihara et al., 53 Heterocycles 359 (2000); Couture
et al., 7 J. Chem. Soc'y 789 (1999); Kihara et al., 48
Heterocycles 2473 (1998); Couture et al., 52 Tetrahedron
4433 (1996); Couturre et al., 37 Tetrahedron Letters 3697
(1996); Natsugari et al., 38 J. Med. Chem. 3106 (1995);
Moehrle et al., 321 Archiv der Pharm. 759 (1988); Gore et
al., 3 J. Chem. Soc'y 481 (1999); Narasimhan et al., 3 J.
Chem. Soc'y, Chem. Commc'ns 191 (1987); Henry et al., 40
J. Org. Chem. 1760 (1975); Berti, 90 Gazzetta Chimica
Italiana 559 (1960); Berti et al., 49 Annali di Chimica 2110,
1253 (Rome, Italy, 1959); WO 2012/000595; Couture et al.,
52 Tetrahedron 4433 (1996); WO 2010/069504; WO 2010/
069504; WO 2006/030032; WO 2005/095384; US 2005/
0222159; WO 2013/064984; Mishra et al., 2013 Eur. J. Org.
Chem. 693 (2013); Vachhani et al., 69 Tetrahedron 359
(2013); Xie et al., 45 Eur. J. Med. Chem. 210 (2010);
Mukaiyama et al., 15 Bioorg. & Med. Chem. 868 (2007); JP
2005/089352; Wang et al., 9 Molecules 574 (2004); WO
2000/023487; US 2006/0287341; CN 103183675; Hares et
al., 32 Egyptian J. Pharm. Sci. 303 (1991); DE 2356005; DE
2133898; DE 2133998; DE 2011970; U.S. Pat. No. 3,816,
422; Staehle et al., 8 Justus Liebigs Annalen der Chem. 1275
(1973). Additional methods for the synthesis of the substituted heterocyclic derivative compounds disclosed herein are readily available to one of skill in the art.

Regarding the synthesis of Compound 1, anhydrous solvents and oven-dried glassware were used for synthetic transformations sensitive to moisture or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For $^1$H NMR spectra, the solvent peak was used as the reference peak.

Step 1: 2-methyl-4-(4,4,5,5-tetramethyl-1,3,2-dioxaborolan-2-yl)isoquinolin-1-one

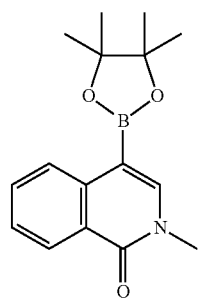 [SMILES: Cn1cc(B2OC(C)(C)C(C)(C)O2)c2ccccc2c1=O]

A suspension of 4-bromo-2-methylisoquinolin-1-one (100 mg, 0.42 mmol), bis(pinacolato)diboron (214 mg, 0.84 mmol), Pd(dppf)Cl$_2$ (31 mg, 0.04 mmol) and potassium acetate (104 mg, 1.05 mmol) in dioxane (2 mL) under nitrogen was heated to 90° C. for 135 min. The mixture was then cooled to room temperature (RT) and diluted with ethyl acetate (8 mL). The mixture was washed with aqueous-saturated solution of NaHCO$_3$ (8 mL) and brine (8 mL). The organic phase was separated, dried over Na$_2$SO$_4$, filtered, and concentrated under reduced pressure. The residue was purified by normal phase column chromatography (10%-90% EtOAc/Hexanes) to give the title compound (44 mg, 37%). $^1$H NMR (CDCl$_3$, 400 MHz) δ 8.43 (d, J=7.9 Hz, 1H), 8.40 (dd, J=8.2 Hz, 0.9 Hz, 1H), 7.68 (s, 1H), 7.65 (ddd, J=8.2, 8.2, 1.1 Hz, 1H), 7.46 (t, J=7.5 Hz, 1H), 3.63 (s, 3H), 1.38 (s, 12H). LCMS: 286 (M+H)$^+$.

Step 2: 4-[2-(cyclopropylmethoxy)-5-methylsulfonylphenyl]-2-methylisoquinolin-1-one

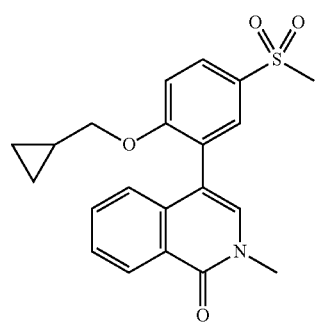 [SMILES: Cn1cc(-c2cc(S(C)(=O)=O)ccc2OCC2CC2)c2ccccc2c1=O]

For about 3 min, N$_2$ was bubbled through a mixture of 2-methyl-4-(4,4,5,5-tetra-methyl-1,3,2-dioxaborolan-2-yl)isoquinolin-1-one (51 mg, 0.14 mmol), 2-bromo-1-(cyclopropyl-methoxy)-4-methylsulfonylbenzene (30 mg, 0.13 mmol), aqueous 1M K$_3$PO$_4$ (0.3 mL) and Pd(dppf)Cl$_2$ (10 mg, 0.013 mmol) in dioxane (1.15 mL), which was then microwaved at 100° C. for 1 hr, and then filtered through a plug of anhydrous Na$_2$SO$_4$ using ethyl acetate to transfer and rinse. Purification by silica gel chromatography, eluting with 5%-50% EA in hexane over 4 min and continuing 50% isocratic EA gave the title compound $^1$H NMR (DMSO-d6, 400 MHz) δ 0.09 (m, 2H), 0.29 (m, 1H), 0.35 (m, 1H), 0.94 (m, 1H), 3.22 (s, 3H), 3.57 (s, 3H), 3.95 (m, 2H), 7.16 (d, J=7.9 Hz, 1H), 7.37 (d, J=8.8 Hz, 1H), 7.53 (m, 2H), 7.65 (t, J=7.6 Hz, 1H), 7.81 (d, J=2.4 Hz, 1H), 7.97 (dd, J=8.8, 2.4 Hz, 1H), 8.30 (d, J=8.1 Hz, 1H). LCMS: 384 (M+H)+.

Alternatively, 4-[2-(cyclopropylmethoxy)-5-methylsulfonylphenyl]-2-methylisoquinolin-1-one can be prepared as follows.

Step 1: 2-methyl-4-(4,4,5,5-tetramethyl-1,3,2-dioxaborolan-2-yl)isoquinolin-1-one

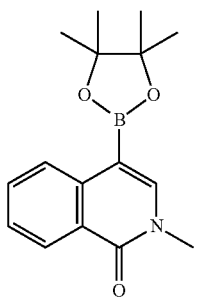 [SMILES: Cn1cc(B2OC(C)(C)C(C)(C)O2)c2ccccc2c1=O]

A mixture of 4-bromo-2-methylisoquinolin-1-one (8.0 g, 33.6 mmol), bis(pinacolato)diboron (17.1 g, 67.2 mmol), KOAc (6.6 g, 67.2 mmol), Pd$_2$(dba)$_3$ (3.1 g, 3.36 mmol) and X-Phos (1.6 g, 3.36 mmol) in anhydrous dioxane (200 mL) was stirred at 60° C. for 12 hr. The reaction mixture was concentrated, and the residue was purified by column chromatography on silica gel (PE:EA=15:1) to give the title compound (6.0 g, 62%) as a solid.

Step 2: 4-[2-(cyclopropylmethoxy)-5-methylsulfonylphenyl]-2-methylisoquinolin-1-one

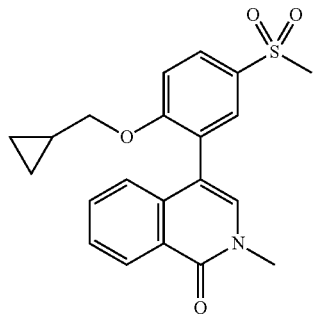 [SMILES: Cn1cc(-c2cc(S(C)(=O)=O)ccc2OCC2CC2)c2ccccc2c1=O]

The title compound from Step 1 (5.0 g, 17.5 mmol), 2-bromo-1-(cyclopropylmethoxy)-4-methylsulfonylbenzene (6.4 g, 21 mmol), $K_3PO_4$ (9.3 g, 43.9 mmol) and $Pd(dppf)Cl_2$ (1.4 g, 1.75 mmol) in a dioxane/water (100 mL/10 mL) mixture were stirred at 60° C. for 12 hr. The reaction mixture was concentrated under reduced pressure and the residue was purified by column chromatography on silica gel (EA:DCM=1:4). Appropriate fractions were combined and concentrated under reduce pressure. The resultant solid was recrystallized from DCM/MTBE (1:1, 50 mL) to give the title compound (4.0 g, 60%) as a white solid. $^1$H NMR: (CDCl3, 400 MHz) δ 8.51 (dd, J1=8.0 Hz, J2=0.8 Hz, 1H), 7.98 (dd, J1=8.4 Hz, J2=2.4 Hz, 1H), 7.86 (d, J=2.4 Hz, 1H), 7.53 (m, 2H), 7.16 (d, J=7.6 Hz, 1H), 7.10 (m, 2H), 3.88 (m, 2H), 3.66 (s, 3H), 3.09 (s, 3H), 1.02-0.98 (m, 1H), 0.44-0.38 (m, 2H), 0.11-0.09 (m, 2H). LCMS: 384.1 $(M+H)^+$. See also U.S. patent application Ser. No. 14/517,705.

Example 2. In Vitro Enzyme Inhibition Assay

Determination of the $IC_{50}$ for the heterocyclic derivative BRD4 inhibitor Compound 1 was performed as follows. His-tagged BRD4 was cloned, expressed, and purified to homogeneity. Filipakopoulos et al., 468 Nature 1067-73 (2010). BRD4 binding and inhibition was assessed by monitoring the interaction of biotinylated H4-tetraacetyl peptide (AnaSpec, H4K5/8/12/16(Ac), biotin-labeled) with the target using the AlphaScreen technology (Life Technologies). In a 384-well ProxiPlate BRD4(BD1) (2 nM final) was combined with peptide (15 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or Compound 1 dilution series in DMSO. After 20 min incubation at RT, Alpha streptavidin donor beads and Nickel Chelate acceptor beads were added to a final concentration of 5 µg/mL. After 2 hr of equilibration, plates were read on an Envision instrument and the $IC_{50}$ was calculated using a four-parameter non-linear curve fit. The ability of Compound 1 to inhibit BRD4 activity was quantified and the respective $IC_{50}$ value was determined. For comparison, a related compound, 2-methyl-4-phenylisoquinolin-1-one, had an $IC_{50}$ of 2.782 µM in this assay. Compound 1 exhibited an $IC_{50}$ value of <0.5 µM in this assay, as shown in Table 1.

Example 3. In Vitro Cell-Based Assay

A colorimetric cellular proliferation assay (Cell-MTS assay) was performed to assess the ability of the heterocyclic derivative BRD4 inhibitors disclosed herein to effect the proliferation of established cancer cell lines.

Assay Principle: The Cell-MTS assay is a 7-day plate-based colorimetric assay that quantifies the amount of newly generated NADH in the presence or absence of test compound. The NADH level is used for the quantification of cancer cell proliferation.

Assay Method: Established cancer cell lines with a variety of driving mutations were obtained from American Type Culture Collection (ATCC) and routinely passaged according to ATCC protocols. For routine assay, these cells were seeded at densities that enabled ~90% confluence after 7 days of culture. Raji, human Burkitts lymphoma cells, (cMYC) were seeded at 15,000 cells per 96-well. HL-60, human proleukemia cells, (NRAS, p16, p53, c-Myc amplified) were seeded at 5,000 cells per 96-well. NCI-H460, human non-small cell lung cancer cells, (KRAS, PIK3CA, STLK11, p16) were seeded at 3,000 cells per 96-well. Plated cells were incubated for 24 hr, and thereafter cells received an 11-point dilution of Compound 1 with final concentration ranges from 100 µM to 2.0 nM. Cells were incubated in the presence of the drug for 168 hr at 37° C., and 5% $CO_2$. At the end of this incubation period, 80 µL of media is removed and 20 µL of CellTiter96®. AQueous Non-Radioactive Cell Proliferation Assay solution (Promega) was added. The cells were incubated until an $OD_{490}$ was >0.6 was reached. $IC_{50}$ values were calculated using the IDBS XLfit software package and include background subtracted $OD_{490}$ values and normalization to DMSO controls. Cellular proliferation $IC_{50}$ values were uploaded and archived using the Chem Biography Platform. Table 1 provides the results of the in vitro enzyme inhibition assay experiments and the in vitro cell-based assay experiments performed with Compound 1.

TABLE 1

In vitro activity of 4-[2-(cyclopropylmethoxy)-5-methylsulfonylphenyl]-2-methylisoquinolin-1-one (Compound 1)

| | BRD4 | Raji | HL-60 | H460 |
|---|---|---|---|---|
| $IC_{50}$ in µM: | ≤0.5 µM | ≤0.5 µM | ≤0.5 µM | >5.0 µM |

Example 4: Preparation of Crystalline Form A Compound 1

Pure fractions from the silica gel column chromatography purification of Compound 1 (60:40 Hex/EtOAc to 100% EtOAc) were collected, filtered through polish filter and concentrated to ~800 mL-1000 mL. The resulting slurry was filtered and washed with a mixture of Hex/EtOAc (50:50, 2×200 mL). The light yellow solid was dried under vacuum at room temperature to afford 128.6 g of purified Compound 1.

A 3-Liter 3-neck round bottom flask equipped with an overhead stirrer, thermocouple, condenser, heating mantle, and nitrogen inlet, was charged with Compound 1 (140.6 g) in filtered THF (840 mL). The slurry was heated to 40° C. to 45° C. and held for 1 hr. The slurry was then filtered and the solids were washed twice with THF (100 and 50 mL).

The solid was dried under vacuum at 30° C.-35° C. to afford 128.4 g of crystalline Compound 1.

Example 5a: XRPD Study of Compound 1

XRPD patterns were also collected on a Bruker AXS D8 Advance diffractometer using Cu Kα radiation (40 kV, 40 mA), θ-2θ goniometer, and divergence of V4 and receiving slits, a Ge monochromator and a Lynxeye detector. The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was packed gently into a cavity cut into polished, zero-background (510) silicon wafer. The sample was rotated in its own plane during analysis. The details of the data collection are: Angular range: 2 2θ to 42° 2θ; Step size: 0.05° 2θ; Collection time: 0.5 s/step. FIG. 1 shows the XRPD diffractogram of Form A Compound 1. Significant XRPD reflection peaks include, but are not limited to, the peaks at 7.8, 9.0, 15.7, 18.0, 21.1, 22.0, 23.6, and 24.5 2θ.

Example 5b: XRPD Study of Amorphous Compound 1

Crystalline Compound 1 (516 mg) was dissolved in dichloromethane (11 mL). Solvents were removed under vacuum (40° C., 30 mbar). The residual solid was further dried under vacuum (25° C., 0 mbar) for 30 min and analyzed by XRPD. The XRPD diffractogram shows no diffraction peaks. FIG. 2 shows the XRPD diffractogram of amorphous Compound 1.

Example 6: Differential Scanning Calorimetry (DSC) Study of Form A Compound 1

Figure 3:
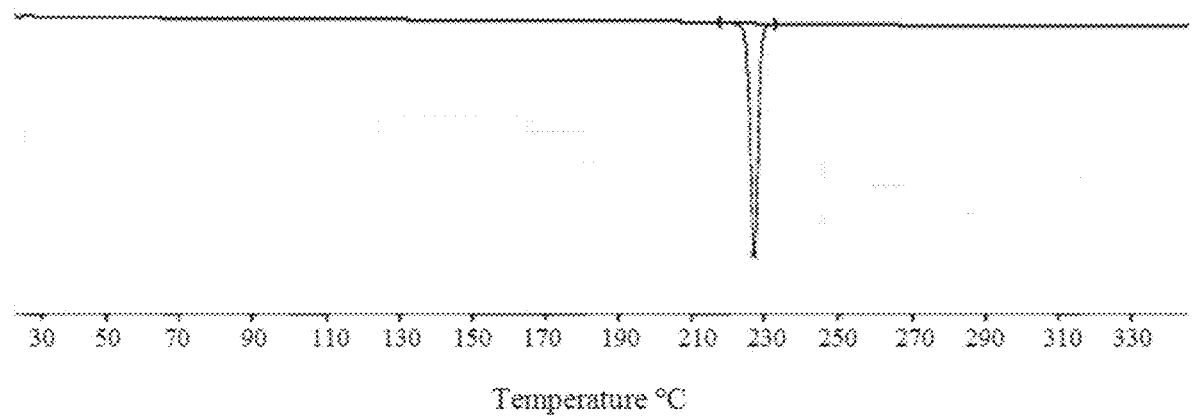
FIG. 3 presents data from a differential scanning calorimetry (DSC) experiment for crystalline form A of 4-[2-(cyclopropylmethoxy)-5-methylsulfonylphenyl]-2-methyl-isoquinolin-1-one (Compound 1).

DSC data were collected on a Mettler DSC 823E equipped with a thirty-four (34) position auto-sampler. The instrument was calibrated for energy and temperature using certified indium. Typically, 0.5 mg-5 mg of each sample (e.g., 4.877 mg), in a pin-holed aluminium pan, was heated at 10° C./min from 25° C. to 350° C. A nitrogen purge at 50 mL/min was maintained over the sample. The instrument control and data analysis software was STARe v12.1. Wg$^{\wedge}$5-1, Integral −599.85 mJ normalized −122.99 Jg$^{\wedge}$-1. Onset was exhibited at 224.33° C.; a sharp endotherm attributable to the melt of the sample appeared at 224.95° C., and is illustrated in FIG. 3.

Example 7: Gravimetric Vapour Sorption (GVS) Study of Form A Compound 1

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0% RH-100% RH), located near the sample. The weight change, (mass relaxation) of the sample as a function of % RH was constantly monitored by the microbalance (accuracy ±0.005 mg).

Figure 4:
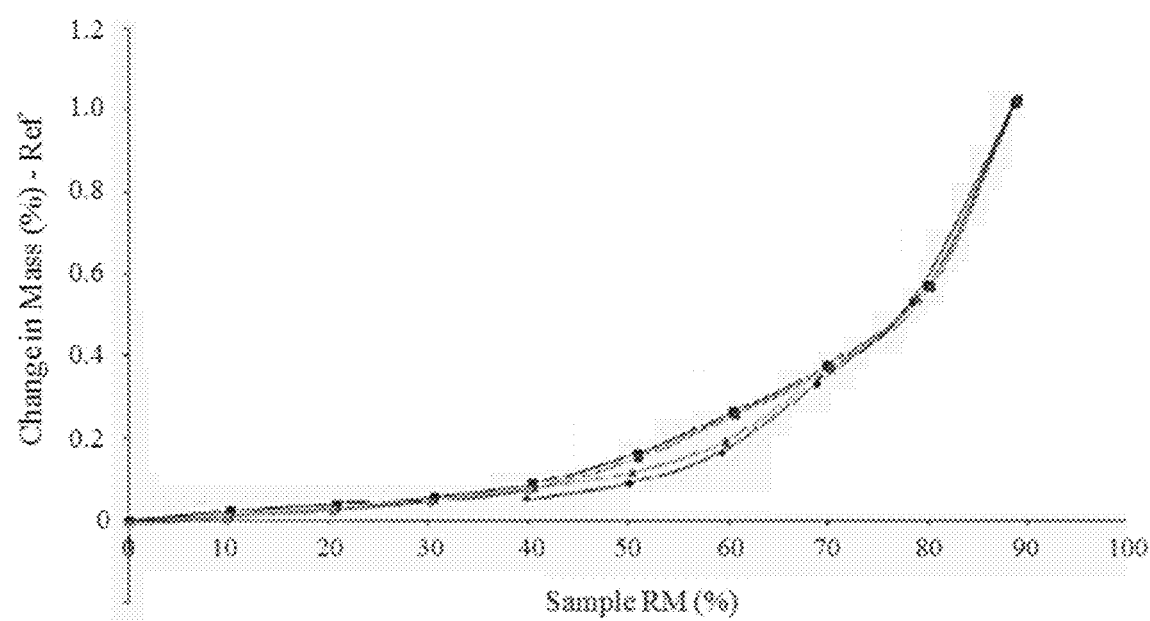
FIG. 4 shows data from a gravimetric vapour sorption (GVS)/(DVS) isotherm plot experiment for crystalline form A of Compound 1. ♦ Cycle 1 Sorp; ■ Cycle 1 Desorp; ▲ Cycle 2 Sorp; □ Cycle 2 Desorp; ■ Cycle 3 Sorp.

Typically 5 mg-20 mg of sample was placed in a tared mesh stainless steel basket under ambient conditions. The sample was loaded and unloaded at 40% RH and 25° C. (typical room conditions). The standard isotherm was performed at 25° C. at 10% RH intervals over a 0% RH-90% RH range. Data analysis was carried out using Microsoft Excel using DVS Analysis Suite v6.2 (or 6.1 or 6.0). FIG. 4 illustrates a graph of the sorption isotherm data.

Example 8: Aqueous Solubility Study of Form A Compound 1

Using the kinetic shake flask method, the solubility of Compound 1 Form A, at pH=7.4 in 50 mM phosphate buffer, was determined to be 2.6 μg/mL-3.7 μg/mL.

Example 9: Pharmacokinetic Study to Determine Dose Proportionality in Rat after Oral Administration of Crystalline Form A of Compound 1

Figure 5:
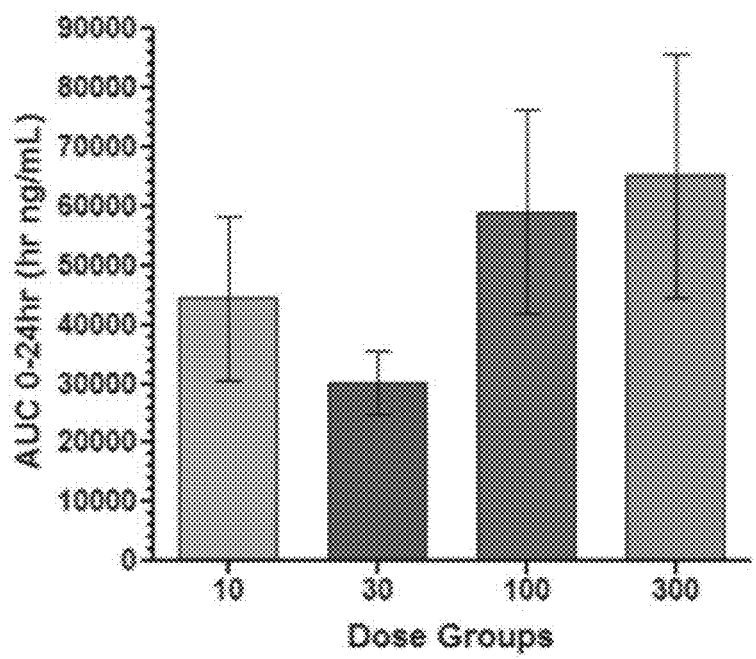
FIG. 5 is a bar graph of AUG 0-20 hr (hr ng/mL) from a full rat pharmacokinetic (PK) study of crystalline form A of Compound 1. Dosing was PO at 10 mg/kg, 30 mg/kg, 100 mg/kg, or 300 mg/kg.

Crystalline Form A of Compound 1 provided non-linear exposure levels (AUC 0-24 hr) when administered orally at 10 mg/kg, 30 mg/kg, 100 mg/kg, or 300 mg/kg to female Sprague Dawley rats as a suspension in 1% Tween, 40% PEG400, and 59% of 0.5% HPMC. A summary of this study is illustrated in FIG. 5.

Example 10: Preparation of Spray-Dried Dispersions of Compound 1

Spray-dried dispersions (SDD) were prepared by mixing a solution of Compound 1 in dichloromethane with either polyvinylpyrrolidone (PVP K12 PF) or hydroxypropyl methylcellulose (Methocel E5 LV) in ratios of Compound 1:polymer of either 1:1 or 1:3, resulting in four unique combinations, followed by spray-drying each preparation using a lab scale Buchi spray dryer (Buchi B290 parameters: inlet T° 80° C.; outlet T° 57° C.; aspirator 100%; nozzle air 30 mm; pump speed 25%; setup: open loop).

Example 11: PK Study to Determine Plasma Exposure Levels in Mouse 6 Hours after Oral Administration of Various SDD Preparations of Compound 1

Figure 6:
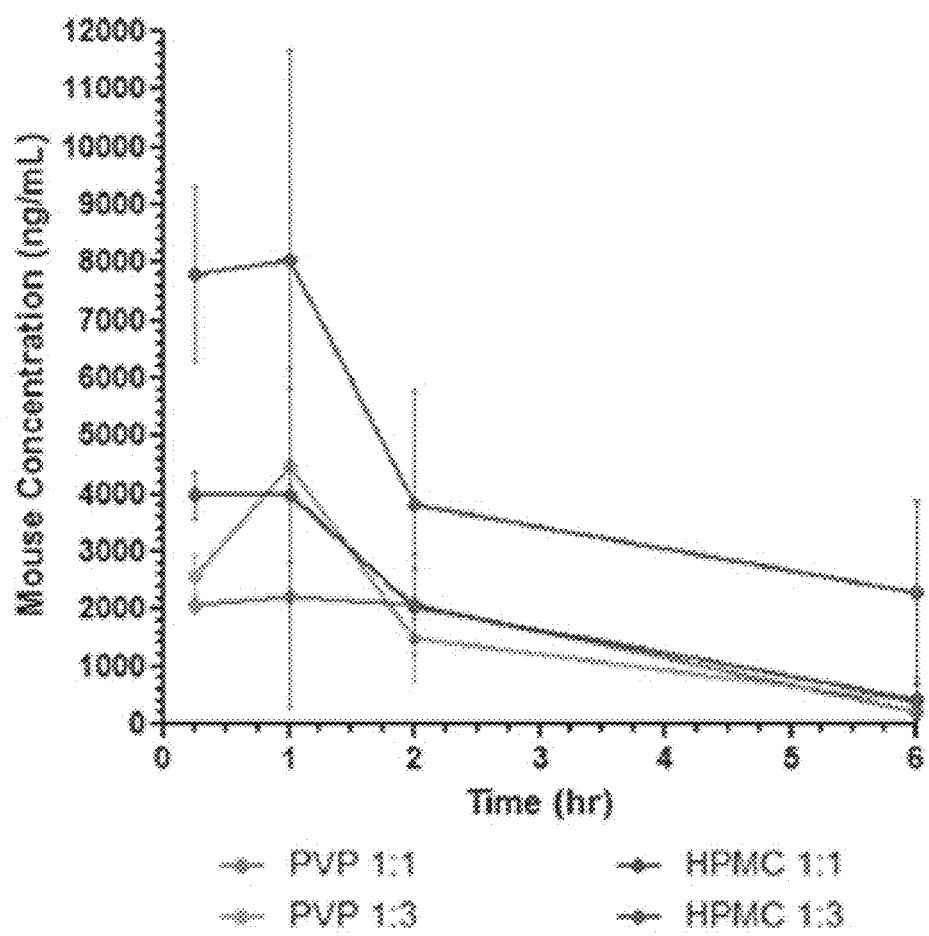
FIG. 6 shows data from a 6 hr mouse PK study in which Compound 1 was processed as a spray dried dispersion (SDD) in four different formulations comprising Compound 1 and polymer.

In order to determine the plasma exposure levels of the four SDDs prepared as described above, each of preparation was administered orally to female CD-1 mice as a suspension in 0.5% MC. FIG. 6 illustrates the results of this experiment. To summarize:

In the composition comprising PVP polymer with a Compound 1:polymer ratio of 1:1,
Compound 1 had a mean AUC 0-6 hr of 7,193 hr ng/mL.
In the composition comprising PVP polymer with a Compound 1:polymer ratio of 1:3,
Compound 1 had a mean AUC 0-6 hr of 8,872 hr ng/mL.
In the composition comprising HPMC polymer with a Compound 1:polymer ratio of 1:1,
Compound 1 had a mean AUC 0-6 hr of 10,484 hr ng/mL.
In the composition comprising HPMC polymer with a Compound 1:polymer ratio of 1:3,
Compound 1 had a mean AUC 0-6 hr of 24,430 hr ng/mL.

Example 12: Preparation of SDD of Compound 1 with HPMC in a Compound 1:Polymer Ratio of 1:3

The spray-dried dispersion was prepared by mixing a solution of Compound 1 in dichloromethane with hydroxypropyl methylcellulose (Methocel E5 LV) (HPMC) in a 1:3 Compound 1:polymer ratio, stirring the mixture overnight, and then spray-drying using a lab scale Buchi spray dryer.

Example 13: XRPD Study of Compound 1) as a SDD with HPMC

Figure 7:
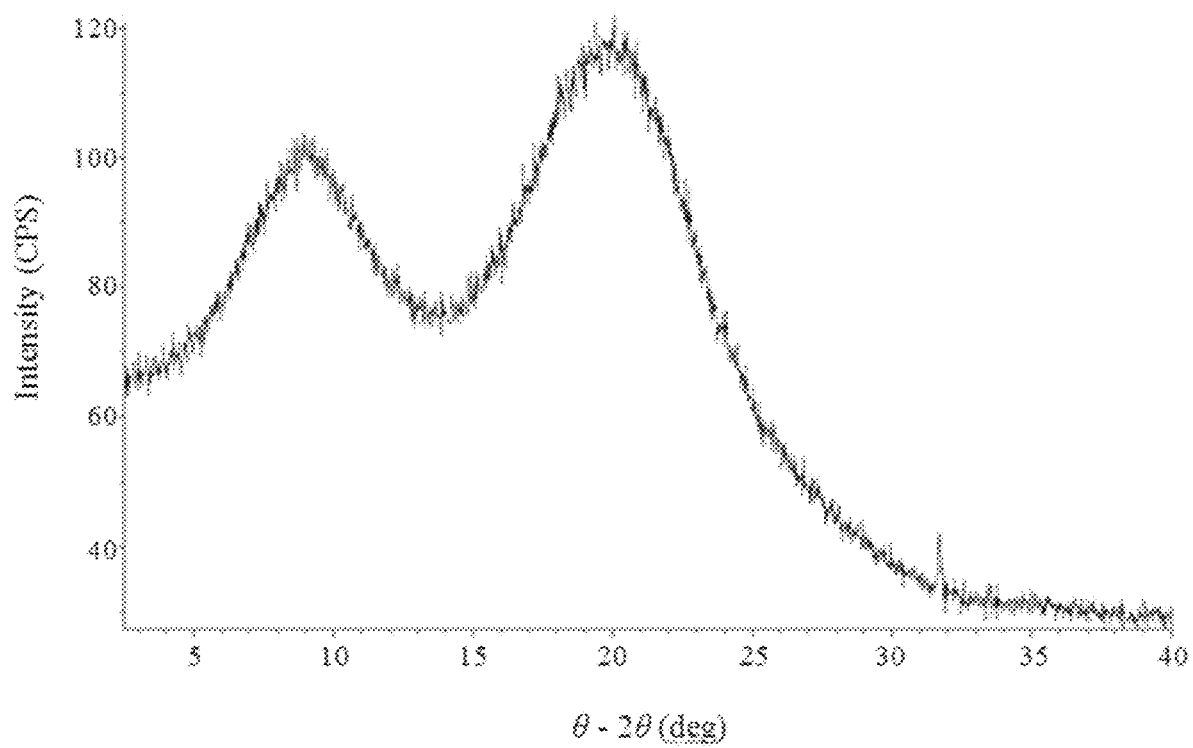
FIG. 7 illustrates an XRPD pattern of amorphous Compound 1 in a SDD.

The XRPD diffractogram of a 25% Compound 1:HPMC (i.e., ratio 1:3) spray-dried dispersion as prepared in Example 12 is shown in FIG. 7.

Example 14: PK Study to Determine Dose Proportionality in Rat or Dog after Oral Administration of SDD of Compound 1

Figure 8A:
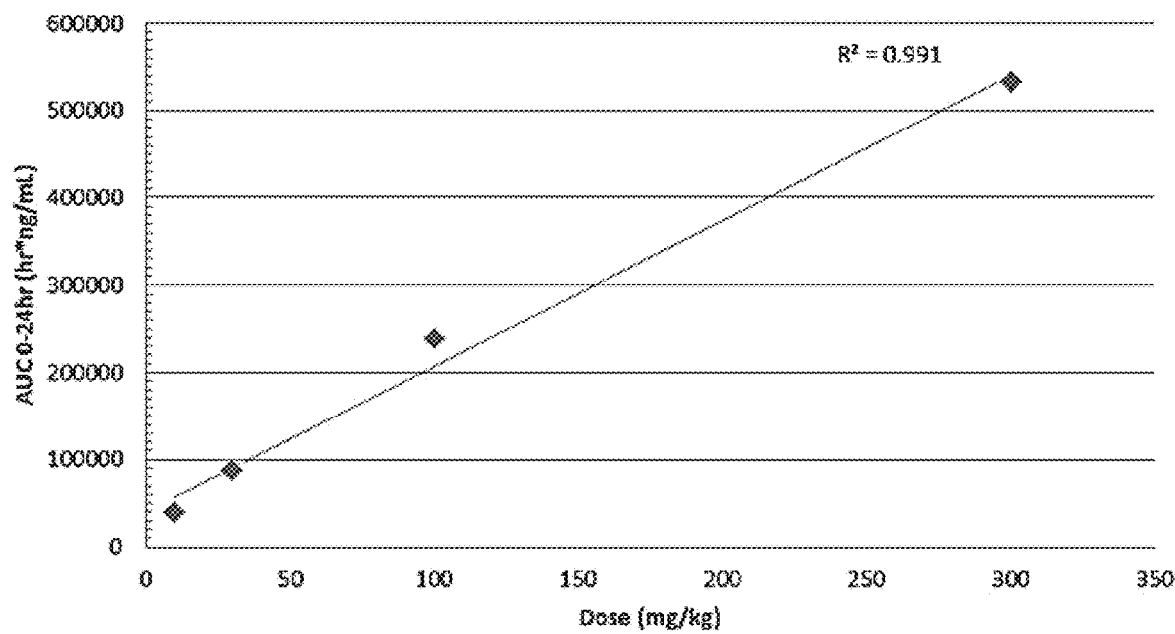
FIG. 8a illustrates a rat PK study using a SDD comprising Compound 1, showing AUC 0-24 hr (hr*ng/mL); dosing by oral administration (PO) at 10 mg/kg, 30 mg/kg, 100 mg/kg, or 300 mg/kg.
Figure 8B:
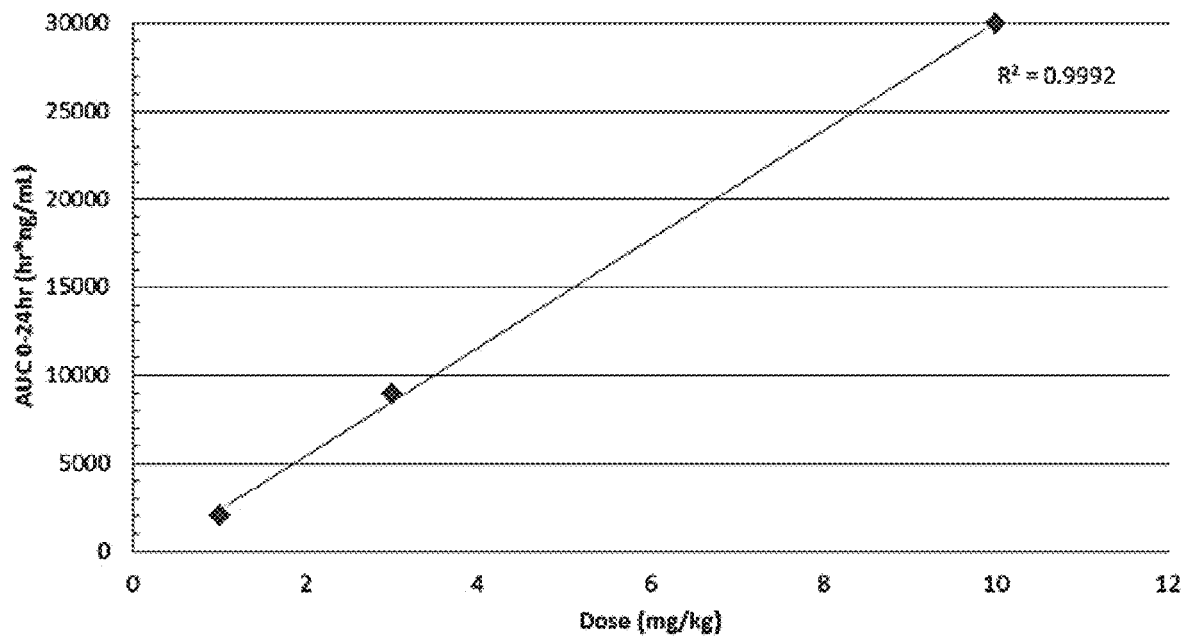
FIG. 8b illustrates a dog PK study using a SDD comprising Compound 1, showing AUC 0-24 hr (hr*ng/mL); dosing PO at 1 mg/kg, 3 mg/kg, or 10 mg/kg.

Compound 1 prepared as a 25% Compound 1:HPMC SDD as described in Example 12 displayed approximate dose proportionality through dose ranges of 10 mg/kg to 300 mg/kg when administered as an oral dosage form (0.5% methylcellulose (MC) suspension) to female Sprague Dawley rats. Results are shown in FIG. 8*a*. Approximate dose proportionality is evidenced through a dose range from 1 mg/kg-10 mg/kg when Compound 1 prepared as a 25% Compound 1:HPMC SDD as described in Example 12 was administered as an oral dosage form (0.5% MC suspension) to male beagle dogs. Results are shown in FIG. 8*b*.

Example 15: Preparation of SDDs of Compound 1 Using Various Grades of HPMCAS Spray-dried dispersions (SDD) were prepared by mixing a solution of Compound 1 in (90:10) acetone:water with hydroxypropylmethylcellulose acetate succinate M or H (HPMCAS-M or HPMCAS-H) in ratios of Compound 1:polymer of either 1:9 or 1:3, followed by spray-drying each preparation using a custom bench scale Lab Spray Dryer (BLD-35; process parameters: inlet T° 93-109° C.; outlet T° 42-43° C.; atomizing pressure 110 psi; feed rate 29 g/min; glass flow rate 450 g/min).

Example 16: PK Study to Determine Plasma Exposure Levels in Rat after Oral Administration of Various SDD Preparations of Compound 1

Figure 9:
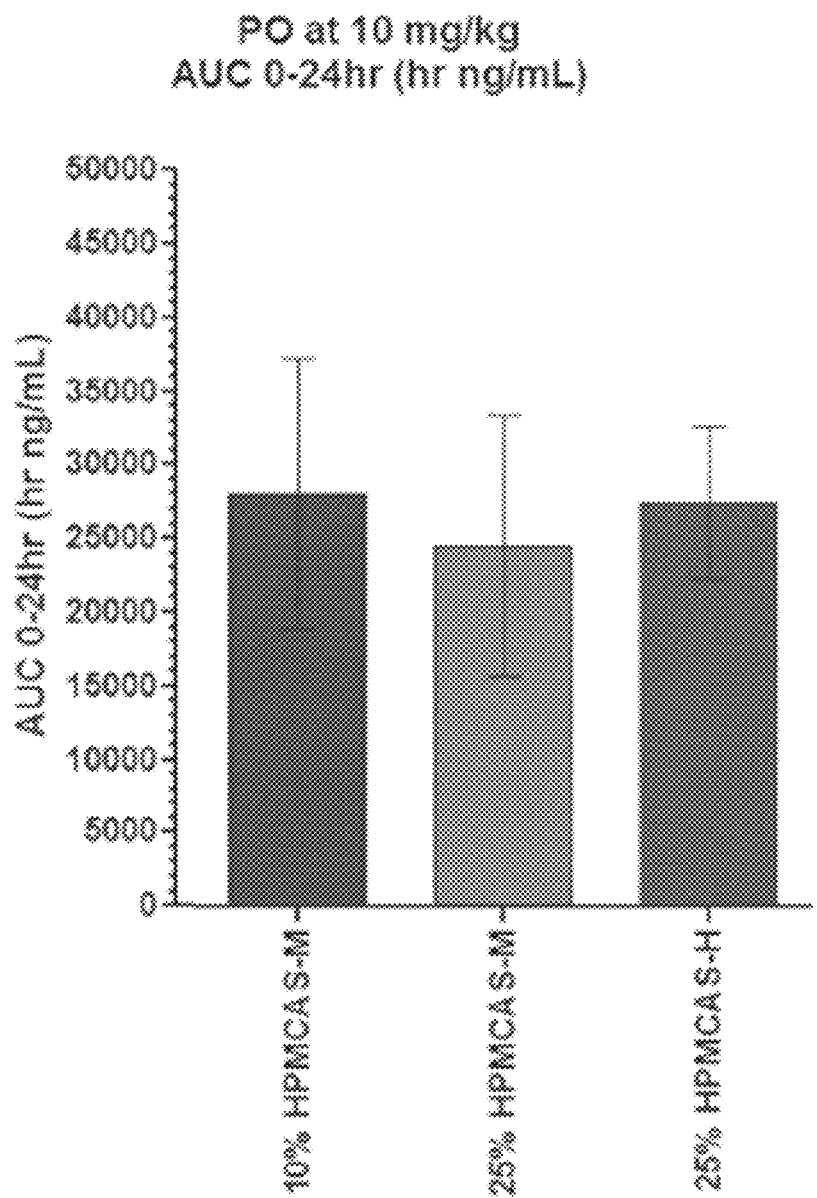
FIG. 9 illustrates plasma exposure levels of Compound 1 in rat after oral administration of various SDD preparations.

In order to determine the plasma exposure levels of the three SDDs prepared as described above, each of them was administered orally at 10 mg/kg (based on Compound 1) to female Sprague Dawley rats as a suspension in 0.5% MC for the 10% HPMCAS-M SDD or as a suspension in 0.5% Methocel A4M/0.5% HPMCAS-HF/20 mM Tris, pH 7.4 for the 25% HPMCAS-M and the 25% HPMCAS-H SDDs. FIG. 9 illustrates the results of this experiment. In the composition comprising HPMCAS-M polymer with a Compound 1:polymer ratio of 1:9, Compound 1 had a mean AUC 0-24 hr of 28,069 hr*ng/mL. In the composition comprising HPMCAS-M polymer with a Compound 1:polymer ratio of 1:3, Compound 1 had a mean AUC 0-24 hr of 24,558 hr*ng/mL. In the composition comprising HPMCAS-H polymer with a Compound 1:polymer ratio of 1:3, Compound 1 had a mean AUC 0-24 hr of 27,469 hr*ng/mL.

Example 17: Preparation of Spray-Dried Dispersions of Compound 1 with HPMCAS-H Spray-dried dispersions (SDD) were prepared by mixing a solution of Compound 1 in (90:10) acetone:water with hydroxypropylmethylcellulose acetate succinate (HPMCAS-HG) in ratios of Compound 1:polymer of either 1:1, 1:2.85, or 1:3, followed by spray-drying each preparation using a custom bench scale Lab Spray Dryer (Bend Research BLD-35; process parameters: inlet T 84-94° C.; outlet T 40-42° C.; atomization pressure 120 psi; nozzle—pressure swirl/Schlick 2.0; solution spray rate 25 g/min; airflow 475 g/min; setup: open loop).

Example 18: Immediate Release Tablet Containing 10 mg of Compound 1

An immediate release tablet containing 10 mg of Compound 1 was generally prepared as follows. The raw materials described in Table 2 (below) were blended, sieved, and blended again prior to granulation. The blended raw materials were granulated using a dry granulation process. Then the dry granulated materials were blended with the extragranular materials. The blended materials were compressed into tablets using 6 mm SRC (standard round concave) tooling.

TABLE 2

| Ingredient | % of tablet | Amount per tablet (mg) |
|---|---|---|
| Intragranular | | |
| SDD 1:3 Compound 1:HPMCAS-HG | 33.33 | 40.0 |
| Microcrystalline cellulose (Avicel PH 101) | 29.34 | 35.2 |
| Lactose (310) | 29.33 | 35.2 |
| Croscarmellose sodium (Ac-Di-Sol) | 6.00 | 7.2 |
| Colloidal Silicon Dioxide (Cabosil M5P) | 0.50 | 0.6 |
| Magnesium stearate | 0.50 | 0.6 |
| Extragranular | | |
| Colloidal Silicon Dioxide (Cabosil M5P) | 0.50 | 0.6 |
| Magnesium stearate | 0.50 | 0.6 |
| Total | 100.00 | 120.0 |

Example 19: Immediate Release Tablet Containing 100 mg of Compound 1

One version of an immediate release tablet containing 100 mg of Compound 1 was generally prepared as follows. The raw materials described in Table 3 (below) were blended, sieved, and blended again prior to granulation. The blended raw materials were granulated using a dry granulation process. Then the dry granulated materials were blended with the extragranular materials. The blended materials were compressed into tablets using concave modified oval tooling (9.1 mm×18.1 mm).

TABLE 3

| Ingredient | % of tablet | Amount per tablet (mg) |
|---|---|---|
| Intragranular | | |
| SDD 1:3 Compound 1:HPMCAS-HG | 50.00 | 400.0 |
| Microcrystalline cellulose (Avicel PH 101) | 21.00 | 168.0 |
| Lactose (310) | 21.00 | 168.0 |
| Croscarmellose sodium (Ac-Di-Sol) | 6.00 | 48.0 |
| Colloidal Silicon Dioxide (Cabosil M5P) | 0.50 | 4.0 |
| Magnesium stearate | 0.50 | 4.0 |
| Extragranular | | |
| Colloidal Silicon Dioxide (Cabosil M5P) | 0.50 | 4.0 |
| Magnesium stearate | 0.50 | 4.0 |
| Total | 100.00 | 800.0 |

Example 20: Immediate Release Tablet Containing 200 mg of Compound 1

One version of an immediate release tablet containing 200 mg of Compound 1 is prepared as follows. The raw materials described in Table (below) are blended, sieved, and blended again prior to granulation. The blended raw materials are granulated using a dryg ranulation process. Then the dry granulated materials are blended with the extragranular materials. The blended materials are the compressed into tablets.

TABLE 4

| Ingredient | % of tablet | Amount per tablet (mg) |
|---|---|---|
| Intragranular | | |
| SDD 1:1 Compound 1:HPMCAS-HG | 50.00 | 400.0 |
| Microcrystalline cellulose (Avicel PH 101) | 21.00 | 168.0 |
| Lactose (310) | 21.00 | 168.0 |
| Croscarmellose sodium (Ac-Di-Sol) | 6.00 | 48.0 |
| Colloidal Silicon Dioxide (Cabosil M5P) | 0.50 | 4.0 |
| Magnesium stearate | 0.50 | 4.0 |
| Extragranular | | |
| Colloidal Silicon Dioxide (Cabosil M5P) | 0.50 | 4.0 |
| Magnesium stearate | 0.50 | 4.0 |
| Total | 100.00 | 800.0 |

We claim:

1. A method for treating cancer or other neoplastic disease, which is selected from the group consisting of Burkitts lymphoma, acute myeloid leukemia (AML), glioblastoma (GBM), and any combination thereof, in a subject in need of such treatment comprising administering to the subject a pharmaceutical composition comprising a spray dried dispersion or a micronized form of 4-[2-(cyclopropylmethoxy)-5-methylsulfonylphenyl]-2-methylisoquinolin-1-one.

2. The method of claim 1, wherein the pharmaceutical composition comprises at least one solid matrix polymer.

3. The method of claim 2, wherein the pharmaceutical composition comprises a solid polymer matrix comprising:
   (a) amorphous 4-[2-(cyclopropylmethoxy)-5-methylsulfonylphenyl]-2-methylisoquinolin-1-one, and
   (b) a polymer selected from polyvinylpyrrolidone, hydroxypropyl methylcellulose, or hydroxypropylmethylcellulose-acetate-succinate;
wherein the solid polymer matrix is a spray dried dispersion.

4. The method of claim 1, wherein the 4-[2-(cyclopropylmethoxy)-5-methylsulfonylphenyl]-2-methylisoquinolin-1-one exhibits XRPD reflection peaks at 7.8, 9.0, 15.7, 18.0, 21.1, 22.0, 23.6 and 24.5 2-theta (2θ).

5. The method of claim 2, wherein the ratio of 4-[2-(cyclopropylmethoxy)-5-methylsulfonylphenyl]-2-methylisoquinolin-1-one to solid matrix polymer is from about 1:1 to about 1:9.

6. The method of claim 2, wherein the ratio of 4-[2-(cyclopropylmethoxy)-5-methylsulfonylphenyl]-2-methylisoquinolin-1-one to solid matrix polymer is about 1:1, about 1:2, about 1:3, about 1:4, about 1:5, about 1:6, about 1:7, about 1:8, or about 1:9.

7. The method of claim 2, wherein the polymer is hydroxypropyl methylcellulose and is present in a ratio of 4-[2-(cyclopropylmethoxy)-5-methylsulfonylphenyl]-2-methylisoquinolin-1-one:polymer of about 1:3.

8. The method of claim 2, wherein the polymer is hydroxypropyl methylcellulose and is present in a ratio of 4-[2-(cyclopropylmethoxy)-5-methylsulfonylphenyl]-2-methylisoquinolin-1-one:polymer of about 1:1.

9. The method of claim 2, wherein the polymer is polyvinylpyrrolidone and is present in a ratio of 4-[2-(cyclopropylmethoxy)-5-methylsulfonylphenyl]-2-methylisoquinolin-1-one:polymer of about 1:3.

10. The method of claim 2, wherein the polymer is polyvinylpyrrolidone and is present in a ratio of 4-[2-(cyclopropylmethoxy)-5-methylsulfonylphenyl]-2-methylisoquinolin-1-one:polymer of about 1:1.

11. The method of claim 2, wherein the polymer is hydroxypropylmethylcellulose acetate succinate and is present in a ratio of 4-[2-(cyclopropylmethoxy)-5-methylsulfonylphenyl]-2-methylisoquinolin-1-one:polymer of about 1:3.

12. The method of claim 2, wherein the polymer is hydroxy-propylmethylcellulose acetate succinate and is present in a ratio of 4-[2-(cyclopropylmethoxy)-5-methylsulfonylphenyl]-2-methylisoquinolin-1-one:polymer of about 1:1.

13. The method of claim 1, wherein the cancer is Burkitts lymphoma.

14. The method of claim 1, wherein the cancer is acute myeloid leukemia (AML).

15. The method of claim 1, wherein the cancer is glioblastoma (GBM).

* * * * *